US011674959B2

(12) United States Patent
Pandey et al.

(10) Patent No.: US 11,674,959 B2
(45) Date of Patent: Jun. 13, 2023

(54) METHODS FOR IDENTIFYING AND PREPARING PHARMACEUTICAL AGENTS FOR ACTIVATING TIE1 AND/OR TIE2 RECEPTORS

(71) Applicants: The Johns Hopkins University, Baltimore, MD (US); AsclepiX Therapeutics, Inc., Baltimore, MD (US)

(72) Inventors: Niranjan Pandey, Baltimore, MD (US); Aleksander S. Popel, Baltimore, MD (US); Jordan J. Green, Baltimore, MD (US); Adam Mirando, Baltimore, MD (US)

(73) Assignees: The Johns Hopkins University, Baltimore, MD (US); AsclepiX Therapeutics, Inc., Baltimore, MD (US)

( * ) Notice: Subject to any disclaimer, the term of this patent is extended or adjusted under 35 U.S.C. 154(b) by 181 days.

(21) Appl. No.: 16/635,862

(22) PCT Filed: Aug. 3, 2018

(86) PCT No.: PCT/US2018/045267
§ 371 (c)(1),
(2) Date: Jan. 31, 2020

(87) PCT Pub. No.: WO2019/028427
PCT Pub. Date: Feb. 7, 2019

(65) Prior Publication Data
US 2021/0132062 A1    May 6, 2021

Related U.S. Application Data

(60) Provisional application No. 62/540,880, filed on Aug. 3, 2017.

(51) Int. Cl.
| | | |
|---|---|---|
| G01N 33/566 | (2006.01) | |
| A61P 27/02 | (2006.01) | |
| A61P 9/00 | (2006.01) | |
| A61K 38/17 | (2006.01) | |
| G01N 33/50 | (2006.01) | |
| A61K 38/39 | (2006.01) | |

(52) U.S. Cl.
CPC ....... *G01N 33/566* (2013.01); *A61K 38/1777* (2013.01); *A61K 38/39* (2013.01); *A61P 9/00* (2018.01); *A61P 27/02* (2018.01); *G01N 33/5008* (2013.01); *G01N 2333/70546* (2013.01); *G01N 2500/02* (2013.01)

(58) Field of Classification Search
None
See application file for complete search history.

(56) References Cited

U.S. PATENT DOCUMENTS

| | | |
|---|---|---|
| 5,475,096 A | 12/1995 | Gold |
| 5,831,012 A | 11/1998 | Nilsson |
| 6,004,746 A | 12/1999 | Brent |
| 6,794,144 B1 | 9/2004 | Saksela |
| 6,818,418 B1 | 11/2004 | Lipovsek |
| 6,994,982 B1 | 2/2006 | Watt |
| 7,166,697 B1 | 1/2007 | Galanis |
| 7,186,524 B2 | 3/2007 | Kolmar |
| 7,250,297 B1 | 7/2007 | Beste |
| 7,417,130 B2 | 8/2008 | Stumpp |
| 7,803,907 B2 | 9/2010 | Stemmer |
| 7,838,629 B2 | 11/2010 | Fiedler |
| 8,507,434 B2 | 8/2013 | Popel |
| 8,557,772 B2 | 10/2013 | Popel |
| 9,051,349 B2 | 6/2015 | Callens et al. |
| 9,056,923 B2 | 6/2015 | Popel et al. |
| 9,802,984 B2 | 10/2017 | Popel et al. |
| 10,106,597 B2 | 10/2018 | Popel et al. |
| 2004/0023334 A1 | 1/2004 | Prior |
| 2004/0132094 A1 | 7/2004 | Etzerodt |
| 2004/0146938 A1 | 7/2004 | Nguyen |
| 2004/0157209 A1 | 8/2004 | Yilmaz |
| 2004/0209243 A1 | 10/2004 | Nixon |
| 2010/0119446 A1 | 5/2010 | Grabulovski |
| 2010/0239633 A1 | 9/2010 | Strome |

(Continued)

FOREIGN PATENT DOCUMENTS

| | | |
|---|---|---|
| WO | 2007/033215 A2 | 3/2007 |
| WO | 2008/085828 A2 | 7/2008 |

(Continued)

OTHER PUBLICATIONS

Saharinen et al., (2017, (Nature Reviews, vol. 16, pp. 635-661) (Year: 2017).*
Eklund et al. Angiopoietin-Tie signalling in the cardiovascular and lymphatic systems. Clin Sci (Lond)., (2017), 131 (1), pp. 87-103.
Saharinen et al. Saharinen P, Eklund L and Alitalo K. Therapeutic targeting of the angiopoietin-TIE pathway. Nat Rev Drug Discov., (2017), 16 (9), pp. 635-661.
Davis et al. Isolation of angiopoietin-1, a ligand for the TIE2 receptor, by secretion-trap expression cloning. Cell., (1996), 87 (7), pp. 1161-1169.
Saharinen et al. Angiopoietins assemble distinct Tie2 signalling complexes in endothelial cell-cell and cell-matrix contacts. Nat Cell Biol., (2008), 10 (5), pp. 527-537.

(Continued)

*Primary Examiner* — Robert S Landsman
(74) *Attorney, Agent, or Firm* — Morgan, Lewis & Bockius LLP

(57) ABSTRACT

The present invention in various aspects and embodiments involves pharmaceutical compositions prepared by contacting a candidate α- or β-integrin-binding molecule, or panel thereof, with an integrin heterodimer, and quantifying heterodimer disruption by the candidate molecule. An integrin-binding molecule, or derivative thereof, that disrupts the integrin heterodimer is selected and is formulated into a pharmaceutical composition for administration to a subject, e.g., who has a disease or disorder related to abnormal vascularization.

15 Claims, 8 Drawing Sheets

Specification includes a Sequence Listing.

(56) References Cited

U.S. PATENT DOCUMENTS

| | | | |
|---|---|---|---|
| 2013/0316950 A1* | 11/2013 | Popel | C07K 14/78 514/13.3 |
| 2015/0125455 A1* | 5/2015 | Green | A61P 5/00 424/139.1 |
| 2016/0122390 A1* | 5/2016 | Popel | B82Y 5/00 435/375 |
| 2016/0176934 A1 | 6/2016 | Roschke et al. | |
| 2017/0183390 A1* | 6/2017 | Springer | C07K 14/70546 |

FOREIGN PATENT DOCUMENTS

| | | |
|---|---|---|
| WO | 2010/132879 A2 | 11/2010 |
| WO | 2012/079088 A2 | 6/2012 |
| WO | 2013/086500 A1 | 6/2013 |
| WO | 2014/197892 A1 | 12/2014 |
| WO | 2017/087825 A1 | 5/2017 |
| WO | 2017087825 | 5/2017 |
| WO | 2018067646 | 4/2018 |
| WO | 2018208829 | 11/2018 |

OTHER PUBLICATIONS

Frye et al. Interfering with VE-PTP stabilizes endothelial junctions in vivo via Tie-2 in the absence of VE-cadherin. J Exp Med., (2015), 212 (13), pp. 2267-2287.
Storz. Intellectual property protection: Strategies for future antibody inventions. MAbs., (2011), 3 (3), pp. 310-317.
Fiedler et al. The Tie-2 ligand angiopoietin-2 is stored in and rapidly released upon stimulation from endothelial cell Weibel-Palade bodies. Blood., (2004), 103 (11), pp. 4150-4156.
Maisonpierre et al. Angiopoietin-2, a natural antagonist for Tie2 that disrupts in vivo angiogenesis. Science., (1997), 277 (5322), pp. 55-60.
Benest et al. Angiopoietin-2 is critical for cytokine-induced vascular leakage. PLoS One., (2013), 8 (8), e70459.
Tabruyn et al. Tabruyn Angiopoietin-2-driven vascular remodeling in airway inflammation. Am J Pathol., (2010), 177 (6), pp. 3233-3243.
Daly et al. Angiopoietin-2 functions as an autocrine protective factor in stressed endothelial cells. Proc Natl Acad Sci USA., (2006), 103 (42), pp. 15491-15496.
Yuan et al. Angiopoietin 2 is a partial agonist/antagonist of Tie2 signaling in the endothelium. Mol Cell Biol., (2009), 29 (8), pp. 2011-2022.
Korhonen et al. Tie1 controls angiopoietin function in vascular remodeling and inflammation. J Clin Invest., (2016), 126 (9), pp. 3495-3510.
Shen et al. Targeting VE-PTP activates TIE2 and stabilizes the ocular vasculature. J Clin Invest., (2014), 124 (10), pp. 4564-4576.
Singh et al. Vascular endothelial growth factor activates the Tie family of receptor tyrosine kinases. Cell Signal., (2009), 21 (8), pp. 1346-1350.
Cascone et al. Stable interaction between alpha5beta1 integrin and Tie2 tyrosine kinase receptor regulates endothelial cell response to Ang-1. J Cell Biol., (2005), 170 (6), pp. 993-1004.
Lee et al. Inhibition of breast cancer growth and metastasis by a biomimetic peptide. Sci Rep., (2014), 4, 7139.
Silva et al. Tyrosine kinase blocking collagen IV-derived peptide suppresses ocular neovascularization and vascular leakage. Sci Transl Med., (2017), 9 (373), eaai8030.
Karagiannis et al. A systematic methodology for proteome-wide identification of peptides inhibiting the proliferation and migration of endothelial cells. Proc Natl Acad Sci USA , (2008), 105 (37), pp. 13775-13780.
Chen et al. Anchorage of VEGF to the extracellular matrix conveys differential signaling responses to endothelial cells. J Cell Biol., (2010), 188 (4), pp. 595-609.
Soldi et al. Role of alphavbeta3 integrin in the activation of vascular endothelial growth factor receptor-2. EMBO J., (1999), 18 (4), pp. 882-892.
Veevers-Lowe et al. Mesenchymal stem cell migration is regulated by fibronectin through alpha5beta1-integrin-mediated activation of PDGFR-beta and potentiation of growth factor signals. J Cell Sci., (2011), 124 (Pt 8), pp. 1288-1300.
Rahman et al. Novel hepatocyte growth factor (HGF) binding domains on fibronectin and vitronectin coordinate a distinct and amplified Met-integrin induced signalling pathway in endothelial cells. BMC Cell Biol., (2005), 6 (1), 8.
Baron et al. Cell adhesion regulates ubiquitin-mediated degradation of the platelet-derived growth factor receptor beta. J Biol Chem., (2000), 275 (50), pp. 39318-39323.
Campochiaro et al. Enhanced Benefit in Diabetic Macular Edema from AKB-9778 Tie2 Activation Combined with Vascular Endothelial Growth Factor Suppression. Ophthalmology., (2016), 123 (8), pp. 1722-1730.
Orfanos et al. Angiopoietin-2 is increased in severe sepsis: correlation with inflammatory mediators. Crit Care Med., (2007), 35 (1), pp. 199-206.
Ziegler et al. Angiopoietin 2 mediates microvascular and hemodynamic alterations in sepsis. J Clin Invest., (2013), pii. 66549.
Han et al. Amelioration of sepsis by TIE2 activation-induced vascular protection. Sci Transl Med., (2016), 8 (335), 335ra355.
Lampugnani et al. The molecular organization of endothelial cell to cell junctions: differential association of plakoglobin, beta-catenin, and alpha-catenin with vascular endothelial cadherin (VE-cadherin). J Cell Biol., (1995), 129 (1), pp. 203-217.
Kontermann. Half-life extended biotherapeutics. Expert Op in Biol Ther., (2016), 16 (7), pp. 903-915.
Dougherty. Unnatural amino acids as probes of protein structure and function. Curr Opin Chem Biol., (2000), 6, pp. 645-652.
Dalton et al., "Constitutive Association of Tie1 and Tie2 with EndothelialIntegrinsis Functionally Modulated by Angiopoietin-1and Fibronectin", PLOS One, 2016, vol. 11, No. 10, pp. 1-24.
Hakanpaa et al., "Endothelial destabilization by angiopoietin-2 via integrin β1 activation", Nat. Commun., 2015, pp. 1-12.
International Search Report and Written Opinion for International Application No. PCT/US2018/045267, dated Nov. 21, 2018, 17 pages.
Jin et al., "Integrins: roles in cancer development and as treatment targets", British Journal Cancer, 2004, vol. 90, No. 3, pp. 561-565.
Kapp et al., "A Comprehensive Evaluation of the Activity and Selectivity Profile of Ligands for RGD-binding Integrins", Sci. Rep., 2017, pp. 1-13.
Koistinen et al., "The Selective Regulation of alphaVβ1 Integrin Expression is Based on the Hierarchical Formation of alphaV-containing Heterodimers", J Biol. Chem., 2002, vol. 277, No. 27, pp. 24835-24841.
Leppanen et al., "Structural basis of Tie2 activation and Tie2/Tie1 heterodimerization", Proc. Natl. Acad. Sci. US A., 2017, vol. 114 No. 17, pp. 4376-4381.

* cited by examiner

METHODS FOR IDENTIFYING AND PREPARING PHARMACEUTICAL AGENTS FOR ACTIVATING TIE1 AND/OR TIE2 RECEPTORS

PRIORITY

This application claims the benefit of and priority to U.S. 62/540,880 filed Aug. 3, 2017, which is hereby incorporated by reference in its entirety.

STATEMENT OF RIGHTS TO INVENTIONS MADE UNDER FEDERALLY SPONSORED RESEARCH

This invention was made with government support under CA138264 and EY026148 awarded by the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ASX-0011PC-SequenceListing_ST25.txt; date recorded: Aug. 3, 2018; file size: 12,387 bytes).

BACKGROUND

Excessive vascular growth and instability are critical pathophysiological events in the progression of several diseases, including wet age-related macular degeneration, diabetic retinopathy, cancer growth and metastasis, and several inflammatory diseases. The angiopoietin-Tie pathway appears to be a major regulator of vascular biology and can be a potential therapeutic target for such diseases. However, therapeutically targeting this pathway is problematic since members of this pathway alternate between having agonistic activities and antagonistic activities, and mechanisms directing such alternations are incompletely understood. Accordingly, there is an unmet need for therapeutics directed to the angiopoietin-Tie pathway and which treat diseases associated with vascular growth and instability.

SUMMARY

The present invention, in various aspects and embodiments, involves pharmaceutical compositions for treating excessive vascular growth (e.g., neovascularization) and vascular instability, including vascular permeability. Excessive vascular growth and vascular instability are pathophysiological events associated with the progression of several diseases, including wet age-related macular degeneration, diabetic retinopathy, cancer growth and metastasis, and inflammatory diseases.

The pharmaceutical agents in accordance with this disclosure are selected for their ability to activate the Tie2 pathway through the disruption of αβ integrin heterodimers, and formulated and/or delivered to patients for treating conditions involving pathological neovascularization and/or vascular permeability or instability. For example, active agents can be selected by contacting a candidate α- or β-integrin-binding molecule, or panel thereof, with an integrin heterodimer, and quantifying αβ-integrin heterodimer disruption by the candidate molecule. An integrin-binding molecule, or derivative thereof, that disrupts the integrin heterodimer is selected and is formulated into a pharmaceutical composition for administration to a subject.

In some embodiments, αβ-integrin heterodimer disruption is determined by quantifying Tie1 and/or Tie2 activation. This may be performed by assaying changes in phosphorylation or activity of Tie1 and/or Tie2 or of signaling molecules associated with Tie1 and/or Tie2, e.g., Akt, STAT3, and/or protein myosin light chain 2 (MLC2), upon contact with the candidate agent. Changes in phosphorylation may be assayed using one or more phospho-specific antibodies. Alternately or additionally, quantifying Tie1 and/or Tie2 activation may be performed by assaying changes in tyrosine kinase activity, e.g., comprising contacting Tie1 and/or Tie2 with an exogenous substrate for phosphorylation in the presence of ATP.

In various embodiments, Tie2 activation is angiopoietin 2 (Ang2)-dependent. For example, Ang2 or peptide or small molecule mimetic thereof can be provided exogenously to assays (or is present endogenously in the assay system) for quantifying Tie2 activation in response to a candidate integrin-binding molecule. In some embodiments, the integrin-disrupting molecule converts Ang2 from an antagonist to a strong agonist of Tie2, which strengthens endothelial cell tight junctions to inhibit vascular leak.

In embodiments, αβ-integrin heterodimer disruption is determined by detecting or quantifying aggregation of Tie1 and/or Tie2, e.g., at an EC cell's surface near a cell-cell junction. Clustering of Tie1 and/or Tie2 at cell junctions may be assayed using at least one antibody comprising a detectable label.

In some embodiments, αβ-integrin heterodimer disruption is determined by detecting or quantifying dissociation of the integrin heterodimer into its α integrin subunit, e.g., α5 and αv, and its β integrin subunit, e.g., β1 and β3. Heterodimer disruption may be determined by detecting or quantifying aggregation of a dissociated α integrin subunit with a Tie2 receptor.

In embodiments, a candidate molecule, or panel thereof, is contacted with the integrin heterodimer in a cell-free system, e.g., using biochemical approaches. In embodiments, a candidate molecule, or panel thereof, is contacted with the integrin heterodimer on the surface of a cell, e.g., cells in a tissue explant or cells grown in culture. In some embodiments, a recombinant cell may include a nucleic acid that expresses an α-integrin subunit which comprises a first detectable label and a nucleic acid that expresses an RTK molecule which comprises a second detectable label. Optionally, the recombinant cell includes a nucleic acid that expresses a β-integrin subunit which comprises a third detectable label. In still other embodiments, one label may be a fluorescent label, and a second label may be a quencher, such that disruption of the heterodimer abrogates quenching of the fluorescent signal, or clustering of the fluorescent label and quencher lead to signal quenching.

The peptide having the amino acid sequence LRRFSTAP-FAFIDINDVINF (SEQ ID NO:2) is referred to herein as AXT107; and is demonstrated to activate the Tie2 pathway by disrupting αβ integrin heterodimers. In embodiments, a candidate molecule is a peptide, including a derivative or AXT107, or comprises an antibody or antibody fragment, small molecule or peptide mimetic.

In some embodiments, a pharmaceutical composition is provided to a mammal to confirm in vivo heterodimer disruption and/or Tie-system activation and/or impact on neovascularization and/or vascular permeability. The active agents and pharmaceutical compositions can be evaluated in animal models as well as in human clinical trials. In such in vivo confirmations, an animal model or human subject may be evaluated for changes to diseased vasculature or vascular stability or permeability.

In the various embodiments described herein, a pharmaceutical composition can be formulated in a variety of forms depending on the desired route and/or dose. Depending on the specific conditions being treated, the pharmaceutical composition may be formulated into liquid or solid dosage forms and administered systemically or locally. The pharmaceutical composition may be formulated, for example, in a timed- or sustained-low release form as is known to those skilled in the art. Suitable routes may include oral, buccal, by inhalation spray, sublingual, ocular, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intrasynovial, intra-hepatic, intralesional, intracranial, intraperitoneal, intranasal, intratumoral, intraocular (e.g., intravitreal) injections, or other modes of delivery.

In embodiments, the pharmaceutical composition comprises a nanoparticle and/or a microparticle. Thus, the pharmaceutical composition includes a nanoparticle and microparticle with the candidate molecule conjugated to the surface of a particle and/or encapsulated within a particle. A nanoparticle and/or microparticle may comprise additional compounds (e.g., a ligand, a targeting moiety (for integrin and/or receptor binding), a candidate molecule derivative, and another therapeutic). Such nanoparticles or microparticles provide a long acting drug depot allowing sustained release of the candidate molecule or compositions comprising the candidate molecule and other compounds.

An aspect of the present invention is a method for treating a disease or disorder comprising administering to a subject, e.g., a human, in need thereof a pharmaceutical composition according to this disclosure. Exemplary diseases treated by the method include, but are not limited to, acute or chronic lung inflammation (e.g., Acute Lung Injury (ALI)), acute respiratory distress syndrome (ARDS), Alzheimer's disease, angioedema, asthma, atherosclerosis, cancer, capillary leak syndrome, cerebral cavernous malformations, cerebral malaria, COPD, diabetic retinopathy, diabetic vascular complications, dry or wet age-related macular degeneration (AMD), hemorrhagic fever, inflammatory disease, influenza (flu), macular degeneration, macular edema, pneumonia, pulmonary edema, Respiratory Syncytial Virus, Retinal Vein Occlusion, SARS, sepsis, multiple sclerosis, urticaria, vascular leak syndrome, vascular permeability associated with organ or tissue transplantation or cancer, and vessel leakage. In some embodiments, the patient has an inflammatory condition involving lymphatic dysfunction, including lymphangitis and lymphedema.

Embodiments of the invention will now be described with reference to the Drawings and following Detailed Description.

DETAILED DESCRIPTION

Figure 1A:
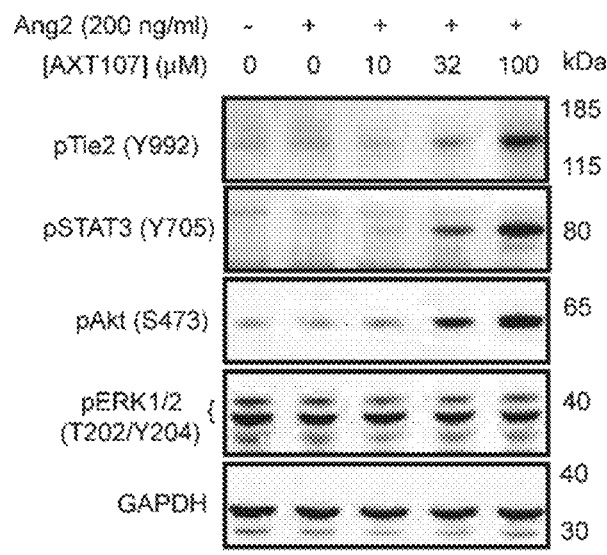
FIG. 1A shows western blots of microvascular endothelial cell (MEC) lysates treated with Ang2 and AXT107 showing phosphorylation of Tie2 and the downstream effectors STAT3, Akt, and Erk1/2, with GAPDH as a loading control.

The present invention, in various aspects and embodiments, involves pharmaceutical compositions for treating excessive vascular growth (e.g., neovascularization) and vascular instability, including vascular permeability. Excessive vascular growth and vascular instability are pathophysiological events associated with the progression of several diseases, including wet age-related macular degeneration, diabetic retinopathy, cancer growth and metastasis, and several inflammatory diseases.

The pharmaceutical agents in accordance with this disclosure are selected for their ability to activate the Tie2 pathway through the disruption of αβ integrin heterodimers, and formulated and/or delivered to patients for treating conditions involving pathological neovascularization and/or vascular permeability or instability. For example, active agents can be selected by contacting a candidate α- or β-integrin-binding molecule, or panel thereof, with an integrin heterodimer, and quantifying αβ-integrin heterodimer disruption by the candidate molecule. An integrin-binding molecule, or derivative thereof, that disrupts the integrin heterodimer is selected and is formulated into a pharmaceutical composition for administration to a subject.

Integrins are transmembrane receptors that are the bridges for cell-cell and cell-extracellular matrix (ECM) interactions. Signal transduction from integrins affect the chemical composition and mechanical status of the ECM, which controls numerous biological responses such as regulation of the cell cycle, cell shape, and/or cell motility; it also affects recruitment of receptors to the cell membrane. This allows rapid and flexible responses to events at the cell surface. There are several types of integrins, and a cell may have several types on its surface. Integrins work alongside other receptors such as cadherins, the immunoglobulin superfamily cell adhesion molecules, selectins, and syndecans to mediate cell-cell and cell-ECM interaction. Ligands for integrins include fibronectin, vitronectin, collagen, and laminin.

The angiopoietin-Tie pathway appears to be a major regulator of vascular biology. In humans, the pathway involves the receptor tyrosine kinase receptors Tie1 and Tie2 (also known as TEK) and three ligands, angiopoietin 1 (Ang1), angiopoietin 2 (Ang2), and the lesser-studied angiopoietin 4 (Ang4). In quiescent vessels, paracrine release of Ang1 from perivascular cells stimulates Tie2 clusters across EC junctions leading to the activation of the anti-apoptotic Akt and reduced permeability through actin rearrangement and dephosphorylation of MLC2 by the Rap1 pathway. Alternatively, stimulation of Tie2 at the EC-ECM interface induces proliferation by ERK1/2 and migratory responses via Dok2 activities.

In contrast to the mostly-consistent Ang1 responses, Ang2 responses are more context-dependent. In inflammatory, diseased, or angiogenic conditions, Ang2 is rapidly released from Weibel-Palade bodies stored within the endothelial cells (ECs), which destabilizes the vasculature by antagonizing the activities of Ang1. This leads to reduced perivascular coverage and either regression or angiogenesis in the absence or presence of other growth factors respectively. However, at low levels of Ang1 or high levels of Ang2, Ang2 may bind and activate Tie2 in manner similar to Ang1. For both ligands, activation of junctional Tie2 enhances association with full-length Tie1 and its cleavage during inflammation is suspected to regulate the agonistic and antagonistic activities of Ang2. However, understanding of the mechanism through which Ang2 switches between agonistic and antagonistic activities remains incomplete.

Both Tie1 and Tie2 (which are RTKs) form complexes with the integrin α5β1 and αvβ3 on the surface of ECs. Interactions between α5β1 integrin and Tie2 ectodomains sensitizes the receptor to activation by Ang1; this is enhanced in the presence of fibronectin. The complexes of an integrin with activated Tie2 stimulate pro-migratory and proliferative downstream pathways associated with FAK, Rac1, and Erk1/2 (MAPK). However, activated Ang1 mediates phosphorylation of the survival-signaling factor Akt; this demonstrates context-specific activation by integrins.

As disclosed herein, binding of a peptide agent (known as AXT107) to an integrin heterodimer disrupts the integrin heterodimer, thereby separating the α-integrin subunit (e.g., α5β1) from the β-integrin subunit (e.g., αvβ3). The separated integrin subunits are then capable of individually interacting with or terminating interactions with receptors (e.g., Receptor Tyrosine Kinases (RTKs)), the receptor's signaling molecules, and/or the integrin's signaling molecules. This mechanism provides a model for screening and selecting other integrin-binding molecules or other active agents that would be useful for activating Tie2 in the therapeutic context through the disruption of the integrin heterodimers.

In some embodiments, αβ-integrin heterodimer disruption is determined by quantifying Tie1 and/or Tie2 activation. This may be performed by assaying changes in phosphorylation or activity of Tie1 and/or Tie2 or of signaling molecules associated with Tie1 and/or Tie2, e.g., Akt, STAT3, and/or protein myosin light chain 2 (MLC2), upon contact with the candidate agent. Changes in phosphorylation may be assayed using one or more phospho-specific antibodies. Alternately or additionally, quantifying Tie1 and/or Tie2 activation may be performed by assaying changes in tyrosine kinase activity, e.g., comprising contacting Tie1 and/or Tie2 with an exogenous substrate for phosphorylation in the presence of ATP.

In some embodiments, the integrin-disrupting molecule converts Ang2 from an antagonist to a strong agonist of Tie2, which strengthens endothelial cell tight junctions to inhibit vascular leak.

As disclosed herein, treatments of cells with an exemplary integrin heterodimer disrupting molecule (AXT107) along with a ligand that activates an RTK (such as Tie 1 and/or Tie2) increases the activity and/or phosphorylation of the RTK. Such treatment also produces changes in activity and/or phosphorylation of those signaling molecules associated with the RTK, i.e., in increase in phosphorylation of some signaling molecules and a decrease in phosphorylation of other signaling molecules.

Exemplary integrin-binding peptides, which can be evaluated and optionally derivatized in accordance with this disclosure, include those described in U.S. Pat. No. 9,056,923, which is hereby incorporated by reference in its entirety. For example, an exemplary integrin-binding peptide comprises the amino acid sequence LRRF-STXPXXXXINNVXNF (SEQ ID NO:1), where X is a standard amino acid or non-natural amino acid. In some embodiments, X at position 7 is M, A, or G; X at position 9 is F, A, Y, or G; X at position 10 is M, A, G, dA, or Nle; X at position 11 is F, A, Y, G, or 4-ClPhe; X at position 12 and position 18 are independently selected from Abu, G, S, A, V, T, I, L or Allyl-Gly. In various embodiments, the peptide contains about 30 amino acids or less, or about 25 amino acids of less, or about 24 amino acids, or about 23 amino acids, or about 22 amino acids, or about 21 amino acids, or about 20 amino acids. In embodiments, an exemplary integrin-binding peptide is a derivative of a peptide of SEQ ID NO:1, in which from one to ten amino acids, such as one, two, or three amino acids of SEQ ID NO:1 are deleted, inserted, or substituted with another standard amino acid, non-natural amino acid, or D-amino acid. In some derivatives of SEQ ID NO:1, amino acids (e.g., from 1 to 10, or from 1 to 5) from the N-terminus are deleted. In some derivatives of SEQ ID NO:1, the peptide contains from one to about five (e.g., 1, 2, and 3) non-natural amino acids. In some derivatives of SEQ ID NO:1, the peptide contains at least one, at least two, or at least three D-amino acids (e.g., from 1 to 10 D-amino acids).

The peptide having the amino acid sequence LRRFSTAP-FAFIDINDVINF (SEQ ID NO:2) is referred to herein as AXT107, and shown to activate the Tie2 pathway through disruption of αβ integrin heterodimers. AXT107 is further described in US 2016/0122390, which is hereby incorporated by reference in its entirety. In some embodiments, the Asp at positions 13 and 16 of SEQ ID NO: 2 is maintained. In some embodiments, the sequence DINDV or NINNV is maintained in the derivative, or is modified by one, two, or three conservative substitutions. Amino acid substitutions can optionally be at positions occupied by an X at the corresponding position of SEQ ID NO:1.

Additional exemplary integrin-binding peptides, and derivatives, are described in U.S. Pat. Nos. 8,557,772; 8,507,434; and WO 2017/087825, each of which is hereby incorporated by reference in its entirety.

In various embodiments, Tie2 activation is angiopoietin 2 (Ang2)-dependent. For example, Ang2 or peptide or small molecule mimetic thereof can be provided exogenously to assays for quantifying Tie2 activation in response to a candidate integrin-binding molecule.

In embodiments, αβ-integrin heterodimer disruption is determined by detecting or quantifying aggregation of Tie1 and/or Tie2, e.g., at an EC cell's surface near a cell-cell junction. Clustering of Tie1 and/or Tie2 at cell junctions may be assayed using at least one antibody comprising a detectable label.

As disclosed herein, treatments with an exemplary integrin-binding molecule along with a ligand that activates an RTK results in the translocation of the RTK from EC-ECM junctions to EC-EC junctions.

In some embodiments, αβ-integrin heterodimer disruption is determined by detecting or quantifying dissociation of the integrin heterodimer into its α integrin subunit, e.g., α5 and αv, and its β integrin subunit, e.g., β1 and β3. Heterodimer disruption may be determined by detecting or quantifying aggregation of a dissociated α integrin subunit with a Tie2 receptor.

As disclosed herein, treatments with AXT107 (an exemplary integrin heterodimer disrupting molecule) along with a ligand for Tie2, disrupts the αβ-integrin heterodimer and separates the α-integrin subunit from the β-integrin subunit. The α-integrin subunit alone complexes with the RTK (e.g., Tie2), whereas the β-integrin subunit becomes distinct from the RTK.

In embodiments, a candidate molecule, or panel thereof, is contacted with the integrin heterodimer in a cell-free system, e.g., using biochemical approaches. In embodiments, a candidate molecule, or panel thereof, is contacted with the integrin heterodimer on the surface of a cell, e.g., cells in a tissue explant or cells grown in culture. In some embodiments, a recombinant cell may include a nucleic acid that expresses an α-integrin subunit which comprises a first detectable label and a nucleic acid that expresses an RTK molecule which comprises a second detectable label. As used herein, the term recombinant cell refers to cells that express at least one recombinant gene. When the α-integrin subunit is complexed with the RTK, there will be co-localization of the first and second detectable labels. The co-localization of the labels also permits visualization of translocation of the RTK from the EC-ECM junction to the EC-EC junction. The first and second detectable labels may also be useful in cell-free experiments, e.g., the labels may be focused upon in co-immuno precipitation experiments. Optionally, the recombinant cell may include a nucleic acid that expresses a β-integrin subunit which comprises a third detectable label. Thus, disruption and separation of the α-integrin subunit from the β-integrin subunit and/or the RTK can be visualized. The third detectable label is also useful in cell-free experiments. In still other embodiments, one label may be a fluorescent label, and a second label may be a quencher, such that disruption of the heterodimer abrogates quenching of the fluorescent signal, or clustering of the fluorescent label and quencher lead to signal quenching.

In various embodiments, detection of integrin heterodimer disruption, and other herein-described detection steps, may comprise one or more of: bimolecular fluorescence complementation (BiFC), BioID (BirA), co-immunoprecipitation, crosslinking protein interaction analysis, dark quenching, detergent (e.g., Triton X-100) fractionation, far-Western blot analysis, fluorescence co-localization, fluorescence resonance energy transfer (FRET), immuno electron microscopy, immuno precipitation, label transfer, proximity ligation assay, e.g., Duolink®, pull-down assays, and split-ubiquitin system, among others.

In various embodiments, integrin heterodimer disruption is determined by assaying narrowing of cell junctions, e.g., by changes in permeability through an intercellular opening, use of an impedance system, e.g., ECIS™, and/or diffusion of a detectable molecule through the intercellular opening. In some embodiments, narrowing of cell junctions may be determined using at least one antibody comprising a detectable label. In some embodiments, heterodimer disruption is determined by detecting formation of and reorganization of cadherin complexes, e.g., complexes comprising VE-Cadherin.

As disclosed herein, treatments with an exemplary integrin heterodimer-disrupting molecule along with a ligand for an RTK (e.g., Tie2) stabilize EC-EC junctions and narrows the junction itself (via reorganization of actin and cadherin) which reduces permeability at the junction. The treatments also strengthen EC-EC junctions through formation of trans interactions with RTKs on adjacent cells.

In some embodiments, a pharmaceutical composition is provided to a mammal to confirm in vivo heterodimer disruption and/or Tie-system activation and/or impact on neovascularization and/or vascular permeability. The active agents and pharmaceutical compositions can be evaluated in animal models as well as human clinical trials. Exemplary animal models include, without limitation, non-human primates, rats, mice, cats, dogs, horses, cattle, cows, pigs, sheep, and rabbits. In some embodiments, the composition is administered to one or more human subjects to evaluate biological effects in a controlled clinical trial. In such in vivo confirmations, an animal model or human subject may be evaluated for changes to diseased vasculature or vascular stability or permeability. Using macular degeneration as an example, a reversal or ceasing of neovascularization is evaluated in the treated animal or subject; additionally, improvements in a visual response may be evaluated in the treated animal or subject. Likewise, in cancer models, reduction in size of a tumor or changes to tumor vasculature or tumor microenvironment may be evaluated.

In some embodiments, the composition is evaluated by intraocular injection (e.g., intravitreal injection) in an animal model of macular edema, diabetic retinopathy, or age-related macular degeneration (dry or wet), for example. In some embodiments, the effect on diseased vasculature can be evaluated by ocular imaging or biochemical analysis of tissue.

In some embodiments, the candidate molecule comprises a small molecule or a library thereof. In some embodiments, the library comprises drug-like, lead-like, peptide-mimetic, or natural product-like molecules. In some embodiments, the library includes integrin-binding molecules, and may further comprise molecules having biological targets such kinases, phosphatases, GPCRs, and proteases, for example.

The candidate molecule may be a peptide or a polypeptide or a derivative thereof. The candidate molecule may include less than about 100 amino acids, less than about 75 amino acids, less than about 50 amino acids, less than about 20 amino acids (e.g., 22, 21, 20, 19, 18, 17, 16, and 15), or less than about 15 amino acids (e.g., 17, 16, 15, 14, 13, 12, 11, 10, 9, 8, 7, 6, 5, 4, and 3). An exemplary peptide-type candidate molecule is AXT107, which may be derivatized in accordance with this disclosure by additions or changes to the amino acid sequence, or in addition or alternatively, conjugation of pendant chemical moieties.

In some embodiments, the candidate molecule is at least a fragment of a ligand (a peptide, polypeptide, or small molecule) that naturally binds an integrin heterodimer, e.g., binds the α-integrin subunit. The candidate molecule may be a derivative of the fragment. The fragment or derivative may include less than about 200 amino acids, less than about 100 amino acids, less than about 50 amino acids, less than about 20 amino acids, or less than about 15 amino acids. The ligand may be derivatized in accordance with this disclosure by additions or changes to the amino acid sequence, or in addition or alternatively, conjugation of pendant chemical moieties.

As used herein a "derivative" differs from a base peptide, polypeptide, or fragment thereof by at least one (e.g., 1, 2, 3, 4, 5, 6, 7, 8, 9, 10, or more) deletions, insertions, and/or substitutions. In some embodiments, the peptide, polypeptide, or fragment thereof includes from 1 to 10 amino acids additions to one or both termini (collectively). In some embodiments, amino acid substitutions are independently selected from conservative or non-conservative substitutions, and may include one or more non-natural amino acids and/or D-amino acids. The term derivative further includes the addition of other chemical moieties, including half-life extension moieties, and targeting moieties.

By non-natural amino acids is meant amino acids that do not occur in nature, but that can be incorporated into a polypeptide chain. Non-natural amino acids include, and are not limited, to 2-aminobutyric acid (Abu), 3-substituted Alanine derivatives, 4-chloro phenylalanine (4-ClPhe), allylglycine (AllyGly), β-amino acids (β$^3$ and β$^2$), Glycine derivatives, Homo-amino acids, Linear core amino acids, N-methyl amino acids, norleucine (Nle), Proline and Pyruvic acid derivatives, Ring-substituted Phenylalanine, and Tyrosine Derivatives, and other non-natural amino acids such as those detailed in Ma, J. S. *Chem. Today* 2003, 65 and Dougherty, D. A. *Curr Opin Chem Biol.* 2000, 6, 645. Amino acid analogs that are known in the art may be employed in the presently-disclosed subject matter.

D-amino acids represent conformational mirror images of L-amino acids. Peptides that contain D-amino acids generally are less susceptible to proteolytic degradation and, thus, are effective longer when used as pharmaceuticals; they can additionally have increased bioavailability in addition to being resistant to proteolysis.

In some embodiments, the candidate molecule is a retro-inverso peptide of a peptide described herein, e.g., of SEQ ID NO:1, SEQ ID NO:2, and its derivatives. Retro-inverso peptides are peptides whose amino acid sequence is reversed and the α-center chirality of the amino acid subunits is inverted as well. For example, a retro-inverso peptide is designed by including D-amino acids in the reverse sequence to help maintain side chain topology similar to that of the original L-amino acid peptide. A retro-inverso peptide can have binding characteristics similar to the L-peptide from which it is derived. Retro-inverso peptides can be used for the study of protein-protein interactions by designing peptidomimetics that mimic the shape of peptide epitopes, protein-protein, or protein-peptide interfaces. Retro-inversopeptides typically are more resistant to proteolytic degradation than the L-peptide from which they are derived and can elicit lower immunogenic responses compared to L-peptides.

Conservative substitutions may be made, for instance, on the basis of similarity in polarity, charge, size, solubility, hydrophobicity, hydrophilicity, and/or the amphipathic nature of the amino acid residues involved. The twenty genetically-encoded amino acids can be grouped into the following six standard amino acid groups: (1) hydrophobic: Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so-modified polypeptide. In addition, glycine and proline may be substituted for one another based on their ability to disrupt α-helices. Some preferred conservative substitutions within the above six groups are exchanges within the following sub-groups: (i) Ala, Val, Leu, and Ile; (ii) Ser and Thr; (ii) Asn and Gln; (iv) Lys and Arg; and (v) Tyr and Phe.

As used herein, "non-conservative substitutions" are defined as exchanges of an amino acid by another amino acid listed in a different group of the six standard amino acid groups (1) to (6) shown above.

Additional peptide derivatives which can be evaluated in accordance with this disclosure (and optionally further derivatized) include LRRFSTAPFAFININNVINF (SEQ ID NO:3), LRRFSTAPFAFIDINDVINW (SEQ ID NO:4), FTNINNVTN (SEQ ID NO:5), or FTDINDVTN (SEQ ID NO:6). As examples, derivatives of the amino acid sequences of SEQ ID NOs: 2 to 6, include, and are not limited to:

(SEQ ID NO: 7)
LRRFSTMPFMF(Abu)NINNV(Abu)NF,

-continued (SEQ ID NO: 8)
LRRFSTMPAMF(Abu)NINNV(Abu)NF, (SEQ ID NO: 9)
LRRFSTMPFAF(Abu)NINNV(Abu)NF, (SEQ ID NO: 10)
LRRFSTMPFMA(Abu)NINNV(Abu)NF, (SEQ ID NO: 11)
LRRFSTMPF(Nle)F(Abu)NINNV(Abu)NF, (SEQ ID NO: 12)
LRRFSTMPFM(4-ClPhe)(Abu)NINNV(Abu)NF, (SEQ ID NO: 13)
LRRFSTMPFMFSNINNVSNF, (SEQ ID NO: 14)
LRRFSTMPFMFANINNVANF, (SEQ ID NO: 15)
LRRFSTMPFMFINININNVINF, (SEQ ID NO: 16)
LRRFSTMPFMFTNINNVTNF, (SEQ ID NO: 17)
LRRFSTMPFMF(AllyGly)NINNV(AllyGly)NF, (SEQ ID NO: 18)
LRRFSTMPFMFVNINNVVNF, (SEQ ID NO: 19)
LRRFSTMPFdAFININNVINF, (SEQ ID NO: 20)
LRRFSTMPFAFININNVINF, (SEQ ID NO: 21)
LRRFSTAPFAFININNVINF, (SEQ ID NO: 22)
LRRFSTAPFdAFIDINDVINF.

(SEQ ID NO: 23)
F(Abu)NINNV(Abu)N (SEQ ID NO: 24)
FTNINNVTN, (SEQ ID NO: 25)
FININNVINF, (SEQ ID NO: 26)
FSNINNVSNF, (SEQ ID NO: 27)
FANINNVANF, (SEQ ID NO: 28)
F(AllyGly)NINNV(AllyGly)NF, (SEQ ID NO: 29)
FVNINNVVNF, (SEQ ID NO: 30)
A(Abu)NINNV(Abu)NF, (SEQ ID NO: 31)
(4-ClPhe)(Abu)NINNV(Abu)NF (SEQ ID NO: 32)
dLRRdLRRFSTAPFAFIDINDVINF, (SEQ ID NO: 33)
dLRRFSTAPFAFIDINDVINdF.

(SEQ ID NO: 34)
FIDINDVINF,

-continued (SEQ ID NO: 35)
FIDINDVINW, (SEQ ID NO: 36)
FTDINDVTN,
or (SEQ ID NO: 37)
LRRFSTAPFAFIDINDVINdF.

Peptides and polypeptides can be chemically synthesized and purified using well-known techniques, such as solid-phase synthesis. See, e.g., U.S. Pat. No. 9,051,349, which is hereby incorporated by reference in its entirety.

In various embodiments, the candidate molecule may comprise a ligand-binding molecule, such as a monoclonal antibody, a polyclonal antibody, a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; an Affimer, a Microbody; an aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', a F(ab')2, or a peptide mimetic, as described in U.S. Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317. For example, an integrin-binding antibody or antigen-binding portion thereof (e.g., single chain variable fragment), can be identified or provided (e.g., by screening a phage display or yeast display library, or otherwise selected from antibodies known in the art). The CDRs or other regions of these molecules responsible for ligand binding or supporting ligand binding activity can be derivatized and screened for integrin disruption or Tie2 activation in accordance with this disclosure.

In the various embodiments described herein, a pharmaceutical composition can be formulated in a variety of forms depending on the desired route and/or dose.

In some embodiments, an effective amount of the candidate molecule will be formulated at a unit dose. For example, for peptide agents a unit dose may be from about 1 μg to about 50 mg per dose, or in some embodiments, from 1 μg to about 1 mg, from about 0.1 mg to about 0.5 mg per dose, or from about 1 to about 10 mg per dose. The exact dosage will depend upon, for example, the route of administration, the form in which the candidate molecule is administered, and the medical condition and/or patient to be treated. For example, a peptide agent (e.g., having 20 amino acids) for intraocular (e.g., intravitreal) injection can be formulated at a unit dose of between 1 μg to 1 mg, while a peptide (e.g., 20 amino acids) for intratumoral injection can be formulated at a unit dose of between 0.1 mg to 25 mg, and, a pharmaceutical composition for intravenous injection can be formulated at a unit dose of between 10 mg to 50 mg. Peptides and polypeptides with more than 20 amino acids or less than 20 amino acids can be formulated at comparative molar amounts. In various embodiments, the candidate molecule is formulated for administration approximately daily, weekly, or monthly, and may employ one or more half-life extending moieties, such as addition of polyethylene glycol (PEG), Fc, or Ig hinge region, or albumin. See, e.g., Kontermann, "Half-life extended biotherapeutics." *Expert Opin Biol Ther.* 2016 July; 16(7): 903-15.

In general, the "effective amount" of candidate molecule or pharmaceutical composition refers to the amount necessary to elicit the desired biological response. As will be appreciated by those of ordinary skill in this art, the effective amount varies depending on such factors as the desired biological endpoint, the candidate molecule or pharmaceutical composition to be delivered, the specific formulation, the target tissue, and the like.

The pharmaceutical composition can include a pharmaceutically acceptable salt, and may include any number of carriers known in the art. The term "pharmaceutically acceptable salt" includes salts that are prepared with relatively nontoxic acids or bases. Pharmaceutically acceptable salts are generally well known to those of ordinary skill in the art. Other pharmaceutically acceptable salts may be found in, for example, "Remington: The Science and Practice of Pharmacy (20$^{th}$ ed.)" Lippincott, Williams & Wilkins (2000).

As used herein, "pharmaceutically acceptable carrier" is intended to include, but is not limited to, water, saline, dextrose solutions, human serum albumin, liposomes, hydrogels, nanoparticles, and microparticles.

Depending on the specific conditions being treated, the pharmaceutical composition may be formulated into liquid or solid dosage forms and administered systemically or locally. The pharmaceutical composition may be delivered, for example, in a timed- or sustained-low release form as is known to those skilled in the art. Techniques for formulation and administration may be found in "Remington: The Science and Practice of Pharmacy (20$^{th}$ ed.)" Lippincott, Williams & Wilkins (2000). Suitable routes may include oral, buccal, by inhalation spray, sublingual, ocular, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, intratumoral, intraocular (e.g., intravitreal) injections, or other modes of delivery.

While the form and/or route of administration can vary, in some embodiments the pharmaceutical composition is formulated for parenteral administration (e.g., by subcutaneous, intravenous, or intramuscular administration).

Powder formulations typically comprise small particles. Suitable particles can be prepared using any means known in the art, for example, by grinding in an airjet mill, ball mill or vibrator mill, sieving, microprecipitation, spray-drying, lyophilization or controlled crystallization. Typically, particles will be about 10 microns or less in diameter. Powder formulations may optionally contain at least one particulate pharmaceutically acceptable carrier known to those of skill in the art. Examples of suitable pharmaceutical carriers include, but are not limited to, saccharides, including monosaccharides, disaccharides, polysaccharides and sugar alcohols such as arabinose, glucose, fructose, ribose, mannose, sucrose, trehalose, lactose, maltose, starches, dextran, mannitol or sorbitol.

Use of pharmaceutically acceptable inert carriers to formulate pharmaceutical compositions disclosed herein into dosages suitable for systemic administration is within the scope of the present invention. With proper choice of carrier and suitable manufacturing practice, the compositions of the present invention, in particular, those formulated as solutions, may be administered parenterally, such as by intravenous injection, or locally, such as intraocular injection. The pharmaceutical compositions can be formulated readily using pharmaceutically acceptable carriers well known in the art into dosages suitable for oral administration. Such carriers enable the pharmaceutical composition to be formulated as tablets, pills, capsules, liquids, gels, syrups, slurries, suspensions and the like, for oral ingestion by a subject (e.g., patient) to be treated.

For injection, pharmaceutical compositions of the present invention may be formulated and diluted in aqueous solutions, such as in physiologically compatible buffers such as Hank's solution, Ringer's solution, or physiological saline buffer.

For nasal or inhalation delivery, the pharmaceutical composition of the present invention also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

In some embodiments, the pharmaceutical composition is formulated for administration directly to the lungs. Local administration to the lungs can be achieved using a variety of formulation strategies including pharmaceutical aerosols, which may be solution aerosols or powder aerosols. Solution aerosols may be prepared using any means known to those of skill in the art, for example, an aerosol vial provided with a valve adapted to deliver a metered dose of the composition. Where the inhalable form of the active ingredient is a nebulizable aqueous, organic or aqueous/organic dispersion, the inhalation device may be a nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer which allows smaller nebulized volumes, e.g. 10 µl to 100 µl.

In embodiments, the pharmaceutical composition comprises a nanoparticle and/or a microparticle. Thus, the pharmaceutical composition includes a nanoparticle and microparticle with the candidate molecule conjugated to the surface of a particle and/or encapsulated within a particle. A nanoparticle and/or microparticle may comprise additional compounds (e.g., a ligand, a targeting moiety (for integrin and/or receptor binding), a candidate molecule derivative, and another therapeutic). Such nanoparticles or microparticles provide a long acting drug depot allowing sustained release of the candidate molecule or compositions comprising the candidate molecule and other compounds.

As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 50 to about 100 nm. In some embodiments, the nanoparticle has a diameter of about 70 to 100 nm.

As used herein, the term "microparticle" includes particles having at least one dimension in the range of at least about one micrometer (µm).

The term "particle" as used herein is meant to include nanoparticles and microparticles.

In some embodiments, the invention provides a nanoparticle comprising PLGA-PEG copolymers and a candidate molecule. In some embodiments, the nanoparticle is synthesized from poly(lactic-co-glycolic acid) polyethylene glycol (PLGA-PEG) block copolymers of tunable size which are covalently linked to the candidate molecule, or other targeting moiety, as described herein. A mix of conjugated and unconjugated polymers in various ratios can create nanoparticles with the desired density of targeting moiety on the surface.

The particles may be designed to provide desired pharmacodynamic advantages, including circulating properties, biodistribution, and degradation kinetics. Such parameters include size, surface charge, polymer composition, ligand conjugation chemistry, peptide conjugation density, among others. For example, in some embodiments, the particles have a PLGA polymer core, and a hydrophilic shell formed by the PEG portion of PLGA-PEG co-polymers, wherein a portion of the PLGA-PEG polymers have a terminal attachment of the candidate molecule. The hydrophilic shell may further comprise ester-endcapped PLGA-PEG polymers that are inert with respect to functional groups, such as PLGA-PEG-MeOH polymers. In some embodiments, some or all of the unconjugated polymers have other terminal groups (such as carboxy) to provide fine tuning of the surface properties.

Candidate molecules in the form of peptides or polypeptides can be chemically conjugated to the particles using any available process. Functional groups for peptide conjugation include PEG-COOH, PEG-NH2, PEG-SH. See, e.g., Hermanson, BIOCONJUGATE TECHNIQUES, Academic Press, New York, 1996. Activating functional groups include alkyl and acyl halides, amines, sulfhydryls, aldehydes, unsaturated bonds, hydrazides, isocyanates, isothiocyanates, ketones, and other groups known to activate for chemical bonding. Alternatively, peptides can be conjugated through the use of a small molecule-coupling reagent. Non-limiting examples of coupling reagents include carbodiimides, maleimides, N-hydroxysuccinimide esters, bischloroethylamines, bifunctional aldehydes such as glutaraldehyde, anhydrides and the like.

In an exemplary embodiment, the nanoparticles have a core (PLGA) that can be tuned for a specific biodegradation rate in vivo (by adjusting the LA:GA ratio and/or molecular weight of the PLGA polymer). In some embodiments, the PLGA is based on a LA:GA ratio of from 20:1 to 1:20, including compositions of L/G of: 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. PLGA degrades by hydrolysis of its ester linkages. The time required for degradation of PLGA is related to the ratio of monomers:the higher the content of glycolide units, the lower the time required for degradation as compared to predominantly lactide units. In addition, polymers that are end-capped with esters (as opposed to the free carboxylic acid) have longer degradation half-lives.

In some embodiments, the PLGA polymers for fabricating nanoparticles have a molecular weight in the range of about 10K to about 70K, such as about 20K, about 25K, about 30K, about 40K, about 50K, about 60K, or about 70K, to provide tunable particle size. In some embodiments, the PLGA polymers used for fabricating microparticles have a molecular weight in the range of about 20K to about 200K, such as from 100K to about 200K. The PEG portion of the polymer is generally in the range of 2K to 5K. In various embodiments, the ratio of PLGA-PEG-peptide and unconjugated PLGA-PEG ranges from about 1:20 to about 20:1, such as from about 1:15 to about 15:1, or about 1:10 to about 10:1, or about 1:5 to about 5:1, or about 1:2 to about 2:1. In some embodiments, the ratio of PLGA-PEG-peptide and unconjugated copolymers is about 1:1. In some embodiments, at least 50% of the polymers have conjugated peptide. In some embodiments, the nanoparticle has a size (average diameter) within the range of about 50 to about 200 nm, or within the range of about 50 to about 100 nm. In some embodiments, the nanoparticle has a zeta potential in deionized water within the range of about −5 mV to about −40 mV, and in some embodiments, from about −10 mV to about −30 mV (e.g., about −20, about −25, or about −30 mV).

While the nanoparticle is substantially spherical in some embodiments, the nanoparticle may optionally be non-spherical.

There are various physical and chemical properties that can affect how a material interacts with a biological system. In the case of microparticle- and nanoparticle-based materials, the choice of material, the size distribution, and the shape distribution of the particles are all critical parameters affecting the particles' activity. It has been shown that both the size and shape of a particle can affect the way the particle interacts with various cells of the body. For example, the shape of the particle can affect how well various cell types can uptake the particle, where an ellipsoidal particle is usually more difficult for a cell to uptake than a spherical particle. Stretching the shape of the particles can therefore reduce unwanted uptake of particles, such as by the immune system cells, thereby extending the half-life of the particles in the body. The size of the particle also affects the ability of cells to uptake and interact with the particles. Optimization of the activity of a particle based system can therefore be achieved by tuning the size and shape distribution of the particles.

In some embodiments, the dimensions of the nanoparticle and/or process for stretching the particles is as disclosed in WO 2013/086500, which is hereby incorporated by reference in its entirety.

In various embodiments, the three-dimensional microparticle or nanoparticle comprises a prolate ellipsoid, wherein the dimension (a) along the x-axis is greater than the dimension (b) along the y-axis, and wherein the dimension (b) along the y-axis is substantially equal to the dimension (c) along the z-axis, such that the prolate ellipsoid can be described by the equation a>b=c. In other embodiments, the ellipsoid is a tri-axial ellipsoid, wherein the dimension (a) along the x-axis is greater than the dimension (b) along the y-axis, and wherein the dimension (b) along the y-axis is greater than the dimension (c) along the z-axis, such that the tri-axial ellipsoid can be described by the equation a>b>c. In yet other embodiments, the ellipsoid is an oblate ellipsoid, wherein the dimension (a) along the x-axis is equal to the dimension (b) along the y-axis, and wherein the dimension (b) along the y-axis is greater than the dimension (c) along the z-axis, such that the oblate ellipsoid can be described by the equation a=b>c. The presently disclosed asymmetrical particles, however, do not include embodiments in which a=b=c.

In still other embodiments, the microparticle or nanoparticle has an aspect ratio ranging from about 1.1 to about 5. In other embodiments, the aspect ratio has a range from about 5 to about 10. In some embodiments, the aspect ratio has a range from about 1.5 to about 3.5.

In some embodiments, the particle is a microparticle that encapsulates a drug cargo (such as a candidate molecule as described herein, with or without other therapeutics).

The particle may contain the candidate molecule conjugated to its surface. In embodiments, when the candidate molecule is a peptide or polypeptide, its N- and/or C-termini may optionally be occupied by another chemical group (other than amine or carboxy, e.g., amide or thiol), and which can be useful for conjugation of other moieties, including PEG or PLGA-PEG co-polymers, as described herein.

Exemplary particle formats include those described in WO 2014/197892, which is hereby incorporated by reference. In some embodiments, particles do not incorporate poly(beta-amino ester) (PBAE), and thus the polymers consist essentially of PLGA-PEG block co-polymers. These particles can be used for intraocular injection, for example, as a treatment for macular degeneration (e.g., wet or dry age-related macular degeneration) or diabetic macular edema.

In some embodiments, a microparticle or nanoparticle comprises a material having one or more degradable linkages, such as an ester linkage, a disulfide linkage, an amide linkage, an anhydride linkage, and a linkage susceptible to enzymatic degradation. In particular embodiments, the microparticle or nanoparticle comprises a biodegradable polymer or blends of polymers selected from the group consisting of poly(lactic-co-glycolic acid) (PLGA), poly(beta-amino ester) (PBAE), polycaprolactone (PCL), polyglycolic acid (PGA), polylactic acid (PLA), poly(acrylic acid) (PAA), poly-3-hydroxybutyrate (P3HB) and poly(hydroxybutyrate-co-hydroxyvalerate). In other embodiments, nondegradable polymers that are used in the art, such as polystyrene, are blended with a degradable polymer or polymers from above to create a copolymer system. Accordingly, in some embodiments, a nondegradable polymer is blended with the biodegradable polymer.

In some embodiments, the nanoparticles contain an additional therapeutic or targeting moiety conjugated to the surface. For example, the nanoparticles may be made from PLGA-PEG-X and PLGA-PEG-Y polymers, where X is a candidate molecule of the present invention and Y is another therapeutic and/or a targeting moiety. The targeting moiety may be a tissue-selective targeting moiety, e.g., which targets ECs or may be selective for diseased cells or cells having a disorder described herein. The targeting moiety may be a monoclonal antibody, a polyclonal antibody, a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; an Affimer, a Microbody; an aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', a F(ab')2, or a peptide mimetic, as described in US Patent Nos. or Patent Publication Nos. U.S. Pat. No. 7,417,130, US 2004/132094, U.S. Pat. No. 5,831,012, US 2004/023334, U.S. Pat. Nos. 7,250, 297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

An aspect of the present invention is a method for treating a disease or disorder comprising administering to a subject, e.g., a human, in need thereof a pharmaceutical composition according to the present disclosure. Exemplary diseases treated by the method include, but are not limited to, acute respiratory distress syndrome, Alzheimer's disease, asthma, atherosclerosis, cancer, cerebral cavernous malformations, cerebral malaria, COPD, diabetic retinopathy, diabetic vascular complications, dry or wet age-related macular degeneration (AMD), hemorrhagic fever, inflammatory disease, influenza (flu), macular degeneration, macular edema, pneumonia, pulmonary edema, Respiratory Syncytial Virus, Retinal Vein Occlusion, SARS, sepsis, vascular permeability associated with organ or tissue transplantation or cancer, vessel leakage, and other diseases or disorders as described herein. Many of the above-mentioned diseases are characterized by microvascular leakage. In embodiments, a pharmaceutical composition comprises a nanoparticle or microparticle including, at least, an encapsulated or conjugated candidate molecule of the present invention for treatment of conditions characterized by microvascular leakage.

In various embodiments, a pharmaceutical composition further includes a second molecule, e.g., AXT107, and/or further includes another therapeutic known to treat a disease or disorder treated by the candidate molecule. The choice of the other therapeutic depends on the disease or disorder to be treated, as described herein.

In some embodiments, the disease or disorder relates to abnormal vascularization, e.g., comprising excessive vascular growth, increased vascular permeability, and/or vascular instability. In various embodiments, the abnormal vascularization is in eye vasculature.

Vascular permeability, often in the form of capillary permeability or microvascular permeability, relates to the capacity of a blood vessel wall to allow for the flow of small molecules (e.g., ions, water, and nutrients) or even whole cells in and out of the vessel. Blood vessel walls are lined by a single layer of endothelial cells. The gaps between endothelial cells, known as tight junctions, are strictly regulated depending on the type and physiological state of the tissue. Increases in vascular permeability can result in edema, a condition characterized by an excess of fluid collecting in the cavities or tissues of the body.

The microvascular endothelium responds to inflammatory and other stimulus, which can play a pivotal role in the pathology of many medical conditions. Diseases and disorders associated with an inflammatory disease include, but are not limited to, atherosclerosis, cancer, cerebral cavernous malformations, diabetic retinopathy, diabetic vascular complications, dry or wet age-related macular degeneration (AMD), macular edema in various retinopathies, sepsis, and/or, vessel leakage.

The potential mediators of vascular permeability, including soluble factors and cellular receptors, and their potential roles and interactions are complex, and can depend on the tissue and particular pathology.

In some embodiments, a pharmaceutical composition of the present invention is administered locally to the lungs, skin, or eyes, to prevent or reduce microvascular leakage or permeability.

In some embodiments, the patient has macular edema. Macular edema occurs when fluid and protein deposits collect on or under the macula of the eye (a yellow central area of the retina) and causes it to thicken and swell. The causes of macular edema include chronic or uncontrolled diabetes type 2 (e.g., diabetic retinopathy), in which peripheral blood vessels including those of the retina leak fluid into the retina. Other causes and/or associated disorders include age-related macular degeneration (AMD), chronic uveitis, atherosclerosis, high blood pressure and glaucoma. In some embodiments, the patient has or is at risk of retinal vein occlusion, which can lead to severe damage to the retina and blindness, due to ischemia and edema. In some embodiments, the patient receives intra-ocular injection of the candidate molecule, pharmaceutical composition, nanoparticle, and/or microparticle. The injection may be in combination with or as an alternative to VEGF blockade therapy.

In other aspects, the invention provides a method for treating cancer, including normalizing the tumor vasculature for chemotherapy, immunotherapy, or other targeted therapy, or preventing or slowing tumor growth or metastasis. Targeting angiogenesis has been shown to be an effective method for treating cancer. VEGF and its receptor VEGFR2 are important mediators of angiogenesis. Bevacizumab, an antibody that sequesters human VEGF, as well as Aflibercept and Ranibizumab, and small molecule tyrosine kinase inhibitors that inhibit VEGFR2, have been administered as treatments for various types of cancer. In addition to its well-known pro-angiogenic activity, VEGF also functions as an immune suppressor by inhibiting the maturation of dendritic cells. Tumors are thought to produce VEGF both to attract neovasculature and to suppress the immune system by reducing the number of mature immune cells and modulating lymphocyte endothelial trafficking. In some embodiments, the cancer is non-responsive to such agents (e.g., after treatment with one or more of such agents), including aflibercept, bevacizumab, ranibizumab, ramucirumab, pazopanib, sorafenib, sunitinib, axitinib, ponatinib, lenvatinib, vandetanib, regorafenib, and cabozantinib.

In some embodiments the cancer is a sarcoma, carcinoma, or solid tumor cancer selected from germ line tumors, tumors of the central nervous system, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, melanoma (including advanced melanoma), renal cancer, bladder cancer, esophageal cancer, cancer of the larynx, cancer of the parotid, cancer of the biliary tract, rectal cancer, endometrial cancer, squamous cell carcinomas, adenocarcinomas, small cell carcinomas, neuroblastomas, mesotheliomas, adrenocortical carcinomas, epithelial carcinomas, desmoid tumors, desmoplastic small round cell tumors, endocrine tumors, Ewing sarcoma family tumors, germ cell tumors, hepatoblastomas, hepatocellular carcinomas, lymphomas, melanomas, non-rhabdomyosarcome soft tissue sarcomas, osteosarcomas, peripheral primitive neuroectodermal tumors, retinoblastomas, rhabdomyosarcomas, and Wilms tumors. In some embodiments, the cancer is non-small cell lung cancer, melanoma, prostate cancer, metastatic renal cell cancer.

Additionally, tumors marshal the immune system to promote their own growth. Recently, many of the mechanisms by which tumors keep the immune system in check have been deciphered. Many types of tumor cells express surface molecules such as PD-L1 and CTLA-4 that interact with receptors on T-cells that invade the tumor to make them quiescent. These discoveries have allowed the development of so-called "checkpoint inhibitors" such as ipilimumab, tremelimumab, nivolumab, and pembrolizumab as cancer drugs. These drugs are antibodies that interrupt the binding of the tumor cells to the cytotoxic T cells thus freeing them from suppression and allowing them to kill the tumor cells. Other therapeutics for checkpoint inhibitors, for which the candidate molecules and pharmaceutical compositions of the present invention may work synergistically, include LAG-3, KIR, OX40L, IDO-1, and TIM-3.

In some embodiments, the cancer is triple negative breast cancer (TNBC), small cell lung cancer (SCLC), glioblastoma, or liver cancer.

In various embodiments, the patient can have either early stage cancer (e.g., stage I or II), or be in later stages (stage III or stage IV). Stage I cancers are localized to one part of the body. Stage II cancers are locally advanced, as are Stage III cancers. Whether a cancer is designated as Stage II or Stage III can depend on the specific type of cancer. For example, stage II can indicate affected lymph nodes on only one side of the diaphragm, whereas stage III indicates affected lymph nodes above and below the diaphragm. The specific criteria for stages II and III therefore differ according to diagnosis. Stage IV cancers have often metastasized, or spread to other organs or throughout the body. The candidate compound or pharmaceutical composition can be administered to prevent progression of Stage I or II cancer, or to slow progression or inhibit further progression of Stage III or Stage IV cancers.

In some embodiments, the cancer is non-resectable, such as non-resectable liver cancer. A non-resectable cancer is a malignancy which cannot be surgically removed, due either to the number of metastatic foci, or because it is in a surgical danger zone.

In some embodiments, the composition is administered to reduce vascular permeability prior to chemotherapy for cancer. For example, a regimen of candidate compound or pharmaceutical composition (e.g., from one to ten doses) may be administered at least one week or at least two weeks prior to receiving cancer chemotherapy, to normalize the tumor vasculature and/or the tumor microenvironment. Exemplary chemotherapeutic agents include aminoglutethimide, amsacrine, anastrozole, asparaginase, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine, among others. In some embodiments, a candidate compound or pharmaceutical composition is formulated for parental administration, including intratumorally in some embodiments.

In some embodiments, the patient has an inflammatory condition involving lymphatic dysfunction, including lymphangitis (an inflammation of the lymph vessels) and lymphedema (a chronic pooling of lymph fluid in the tissue, which can be a side-effect of some surgical procedures. The lymphatic system performs three major functions in the body: drainage of excess interstitial fluid and proteins back to the systemic circulation; regulation of immune responses by both cellular and humoral mechanisms; and absorption of lipids from the intestine. Lymphatic disorders are seen following malignancy, congenital malformations, thoracic and abdominal surgery, trauma, and infectious diseases. Many lymphatic disorders are encountered in the operating theatre and critical care settings. Administration of candidate compound or pharmaceutical composition can help restore, or prevent continued decline of, lymphatic vessel integrity.

In some embodiments, the condition is capillary leak syndrome. Systemic capillary leak syndrome is a condition in which fluid and proteins leak out of capillary vessels and flow into surrounding tissues, resulting in dangerously low blood pressure. Attacks frequently last for several days and require emergency care.

In some embodiments, the condition is sepsis. Sepsis is a life-threatening condition that arises when the body's response to infection injures its own tissues and organs. Sepsis is caused by an immune response triggered by an infection. The infection is most commonly bacterial, but it can be from fungi, viruses, or parasites. Common locations for the primary infection include lungs, brain, urinary tract, skin, and abdominal organs. Sepsis is usually treated with intravenous fluids and antibiotics. Disease severity partly determines the outcome, with a high risk of death. Administration of candidate compound or pharmaceutical composition can help restore, or prevent continued decline of, vascular integrity to ameliorate the condition.

In some embodiments, the condition involves acute or chronic lung inflammation, such as acute respiratory distress syndrome (ARDS), Acute Lung Injury (ALI), chronic asthma, or chronic obstructive pulmonary disorder (COPD). In such embodiments, a candidate compound or pharmaceutical composition may be administered locally by inhalation or administered systemically.

Acute respiratory distress syndrome (ARDS) is characterized by widespread inflammation in the lungs, and may be triggered by pathologies such as trauma, pneumonia and sepsis. ARDS is a form of pulmonary edema provoked by an acute injury to the lungs that result in flooding of the microscopic air sacs responsible for the exchange of gases with capillaries in the lungs. In ARDS, these changes are not due to heart failure. The clinical syndrome is associated with pathological findings including pneumonia, eosinophilic pneumonia, cryptogenic organizing pneumonia, acute fibrinous organizing pneumonia, and diffuse alveolar damage (DAD). Of these, the pathology most commonly associated with ARDS is DAD, which is characterized by a diffuse inflammation of lung tissue. The triggering insult to the tissue usually results in an initial release of chemical signals and other inflammatory mediators secreted by local epithelial and endothelial cells. Inflammation, such as that caused by sepsis, causes endothelial dysfunction, fluid leakage from the capillaries and impaired drainage of fluid from the lungs. Elevated inspired oxygen concentration often becomes necessary at this stage, and may facilitate a 'respiratory burst' in immune cells. In a secondary phase, endothelial dysfunction causes cells and inflammatory exudate to enter the alveoli. This pulmonary edema increases the thickness of the alveolocapillary space, increasing the distance the oxygen must diffuse to reach the blood, which impairs gas exchange leading to hypoxia, increases the work of breathing and eventually induces fibrosis of the airspace.

In some embodiments, the patient has non-cardiogenic pulmonary edema, which is optionally associated with asthma or chronic obstructive pulmonary disorder (COPD).

In some embodiments the condition is angioedema or urticaria. Angioedema is the rapid swelling of the dermis, subcutaneous tissue, mucosa and submucosal tissues. Urticaria, commonly known as hives, occurs in the upper dermis. Cases where angioedema progresses rapidly are a medical emergency, as airway obstruction and suffocation can occur. In some embodiments, administration of candidate compound or pharmaceutical composition may reduce the severity of the symptoms.

In some embodiments, the patient has vascular leak syndrome, which is optionally side effect of immunotherapy or other therapeutic treatment. Capillary leak syndrome is characterized by self-reversing episodes during which the endothelial cells which line the capillaries are thought to separate for a few days, allowing for a leakage of fluid from the circulatory system to the interstitial space, resulting in a dangerous hypotension (low blood pressure), hemoconcentration, and hypoalbuminemia.

Another aspect of the present invention is a recombinant cell including a nucleic acid that expresses an α integrin subunit which comprises a first detectable label and a nucleic acid that expresses a Tie2 molecule which comprises a second detectable label. In some embodiments, the recombinant cell further includes a nucleic acid that expresses a β integrin subunit which comprises a third detectable label. As discussed above, such recombinant cells are useful for cell-free assays, e.g., using biochemical approaches, and for assays in which a candidate molecule, or panel thereof, is contacted with the integrin heterodimer on the surface of a cell, e.g., a cell in a tissue explant and an isolated cell grown in culture.

Any aspect or embodiment described herein can be combined with any other aspect or embodiment as disclosed herein.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example, within plus or minus 10%.

This invention is further illustrated by the following non-limiting examples.

EXAMPLES

Regulatory functions of integrins on Ang-Tie signaling are described in these examples using an exemplary integrin-binding, biomimetic peptide, AXT107, as a model. AXT107 is a twenty-mer peptide, derived from a sequence in type IV collagen. AXT107 binds tightly to integrin $\alpha_5\beta_1$ and to integrin $\alpha_v\beta_3$ and disrupts activities of, at least, the growth factor receptors VEGFR2, cMet, PDGFRβ, and IGF1R (Lee et al., *Sci Rep.* 2014; 4:7139; Lima et al., Sci Transl Med. 2017; 9(373)). AXT107 disrupts interactions between IGF1R and β1 integrin and enhances VEGFR2 degradation in vitro and inhibits the growth and permeability of neovasculature in vivo. The following examples demonstrate that treatment with the exemplary integrin-binding, biomimetic peptide potentiates the normally weak agonistic activity of Ang2 towards Tie2 both in vitro and in vivo and specifically activates downstream targets associated with EC survival and barrier function. Mechanistically, AXT107 treatment dissociates $\alpha_5$ integrin and $\beta_1$ integrin, resulting in the translocation and activation of Tie2 at EC-EC junctions and decreased monolayer permeability through the reorganization of F-actin and VE-cadherin.

Example 1: AXT107 Potentiates the Activation of Tie2 by Ang2

In this example, a regulatory function of integrins on Ang-Tie signaling was investigated using an exemplary integrin-binding, biomimetic peptide, AXT107, as a model.

To investigate the effects of the integrin inhibitor AXT107 on Tie2 signaling, confluent monolayers of microvascular endothelial cells (MECs) on fibronectin-coated dishes were treated with various concentrations of AXT107 followed by exposure to the Tie2 ligands Ang1 or Ang2. Ang1 alone induced phosphorylation of Tie2 (data not shown) whereas Ang2 showed insignificant effects by itself (FIG. 1A and FIG. 1B).

Figure 1B:
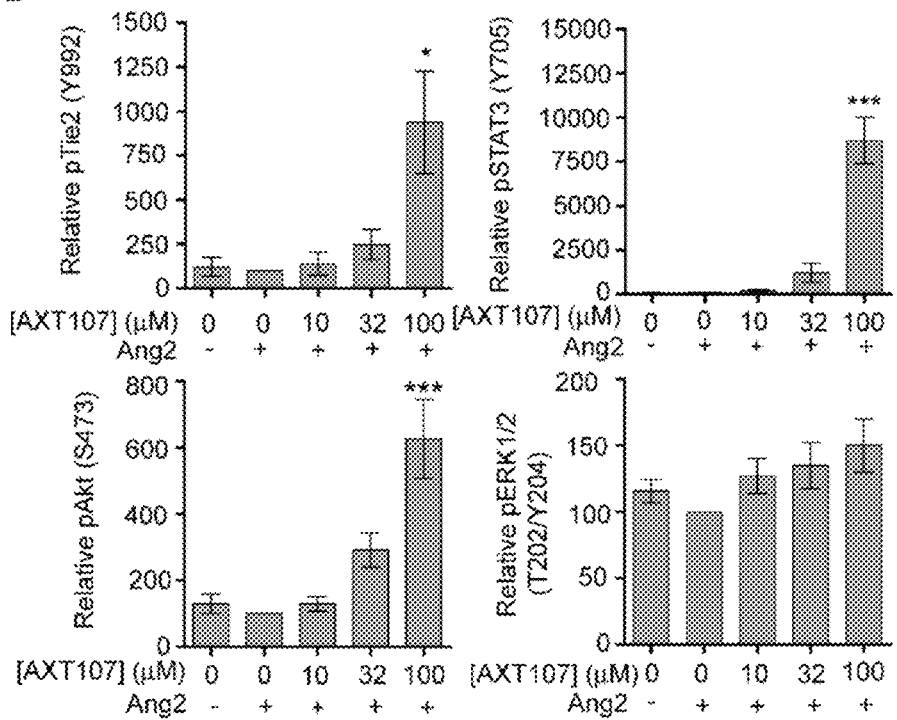
FIG. 1B shows graphs illustrating densitometric analyses of the western blots disclosed in FIG. 1A and adjusted for loading control and presented relative to Ang2-alone control. One-way ANOVA; N=3; *, *** p≤0.05 and 0.001, respectively, relative to Ang2-alone control.

Surprisingly, whereas AXT107 treatment did not significantly influence Ang1 activity (data not shown), a significant, dose-dependent increase in Tie2 phosphorylation was observed in cells treated in combination with AXT107 and Ang2 (FIG. 1A, first row, and FIG. 1B, top left graph). The phosphorylation of the downstream, pro-survival effectors STAT3 and Akt also increased with Ang2 and AXT107 treatment (FIG. 1A, second and third rows, and FIG. 1B, top right and bottom left graphs). However, the phosphorylation of proliferation-associated factor Erk1/2 remained constant in all tested conditions (FIG. 1A, fourth row and FIG. 1B, bottom right graph). For all cases, the total protein levels of Tie2 and the downstream targets remained unchanged (data not shown) and phosphorylation was not induced by peptide alone in absence of either ligand.

Integrin inhibition by AXT107 significantly decreases receptor phosphorylation and downstream signals for many RTKs, e.g., VEGFR2, c-Met, IGF1R, and PDGFRβ, as well as reduced total receptor levels through increased receptor degradation (Lee et al., *Sci Rep.* 2014; 4:7139; Lima et al., *Sci Transl Med.* 2017; 9(373). In contrast, AXT107 clearly potentiates the activation of Tie2 by Ang2 both in vitro and in vivo and does not influence total levels of Tie2, suggesting that increased degradation of the receptor does not occur for Tie2 as it does with other RTKs.

These data demonstrate that treatment with the exemplary integrin-binding, biomimetic peptide potentiates the normally weak agonistic activity of Ang2 towards Tie2, or converts Ang2 from Tie2 antagonist to agonist. Accordingly, AXT107 specifically activates downstream targets associated with endothelial cell (EC) survival and barrier function.

Example 2: Changes in Tie2 Cellular Distribution Mediated by AXT107 Influences Receptor Activation The discovery that AXT107 potentiates Ang2-mediated phosphorylation of Akt and STAT3 but does not potentiate ERK1/2 phosphorylation, suggests that AXT107 specifically activates junctional Tie2 rather than Tie2 molecules at the cell-extracellular matrix (ECM) interface. As such, subsequent experiments evaluate the effects of AXT107 at cell-cell junctions in MEC monolayers using immunofluorescence microscopy rather than at the EC-ECM interface.

Figure 2A:
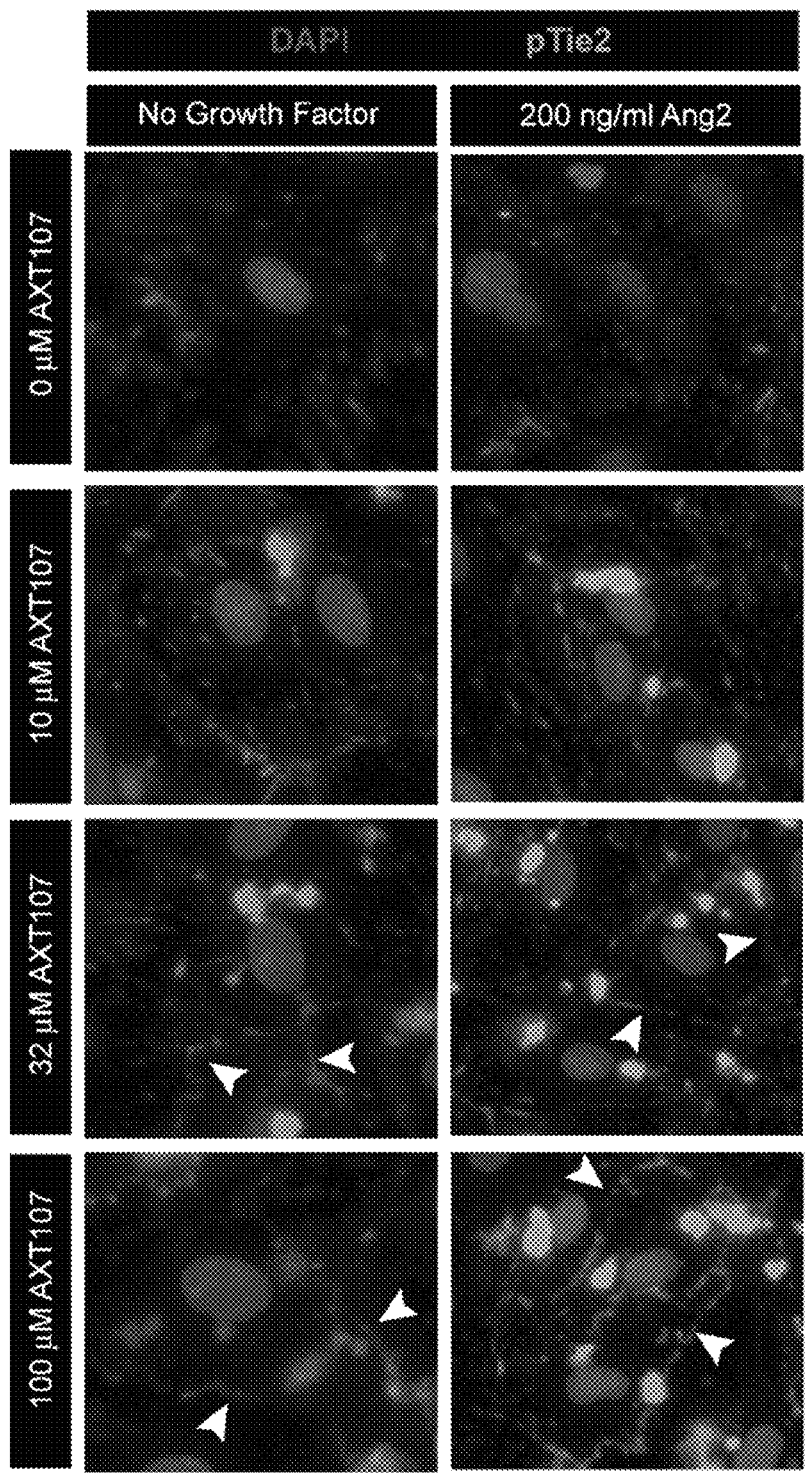
FIG. 2A shows immunofluorescence images of MEC monolayers treated with 0.1% BSA in PBS (left column) or 200 ng/ml Ang2 (right column) for fifteen minutes at varying concentrations of AXT107 and stained for phospho-Tie2 (Y992) (green) and DAPI (blue). White arrows indicate junctional Tie2.

AXT107 was found to self-assemble into peptide complexes when added to media; this behavior is similar to the depots reported in mouse eyes (Lima et al., Sci Transl Med. 2017; 9(373)). In samples treated with Ang2 alone (FIG. 2A, top row), phospho-Tie2 was predominantly found in weak, punctate distributions across the cell surface. Samples treated with Ang2 and AXT107 had increased overall fluorescence intensity and redistributed phospho-Tie2 along cell-cell junctions and into large clusters that co-localized with the AXT107 peptide complexes (FIG. 2A, bottom three rows). These large clusters of phospho-Tie2 are unlikely the result of non-specific interactions between the AXT107 peptide complexes and the tested antibodies as no green fluorescence signal was observed for peptide complexes in regions devoid of cells or in wells treated with secondary antibodies alone (data not shown). Previous reports have emphasized the importance of clustering in Ang2's activation of Tie2 and may explain the potentiation of Tie2 phosphorylation by Ang2 and the activation of downstream effectors of vessel stability and quiescence.

Tie2 at EC-EC junctions form actin-rich complexes that are insoluble in Triton X-100-based lysis buffers but are soluble when distributed over the surface of the cell. Therefore, MEC monolayers were treated with various combinations of AXT107, Ang1, and Ang2 and cell lysates were fractionated by their solubility in Triton X-100-based lysis buffers. Experiments including $VEGF_{165}$ were also performed since VEGFR2 signaling often opposes the activities of Tie2. In each experiment, 100 μM AXT107 was used since it provided clear results relative to lower concentrations of AXT107.

Figure 2B:
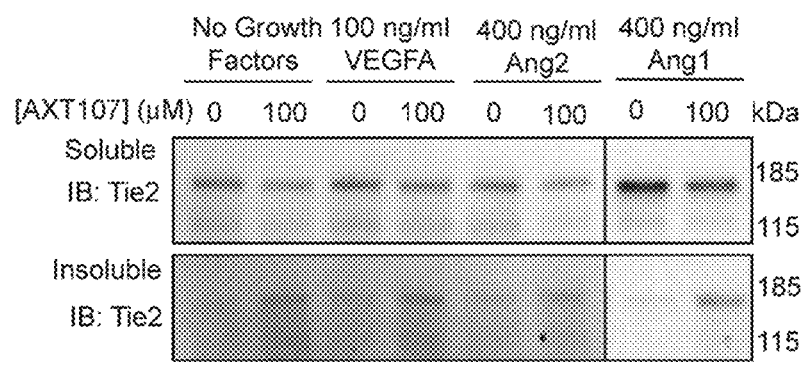
FIG. 2B includes western blots of MEC lysates treated with various growth factors and 100 µM AXT107 or DMSO vehicle and fractioned into Triton X-100-soluble and Triton X-100-insoluble pools.
Figure 2C:
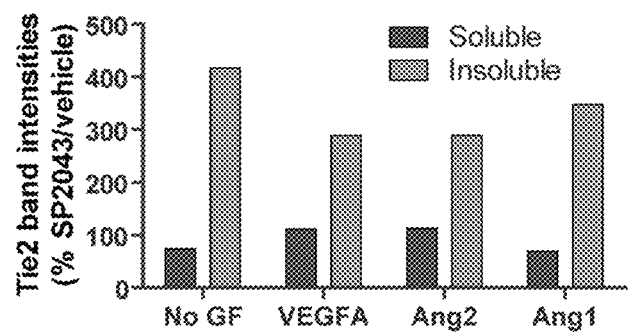
FIG. 2C is a graph illustrating densitometric analyses of the western blots disclosed in FIG. 2B; each bar represents the percent change of AXT107-treated samples relative to the corresponding vehicle control of the same growth factor and separated by soluble (left bars) and insoluble (right bars).

Consistent with the observations from the immunofluorescence assays (as shown in FIG. 2A), increased amounts of Tie2 were found in the insoluble fraction of lysates treated with AXT107; the increased amounts were independent of the specific growth factor treatment (FIGS. 2B and 2C). Similar results were also obtained for Tie1 (data not shown), a co-receptor recently shown to be essential for the activation of junctional Tie2 (Korhonen et al., *J Clin Invest.* 2016; 126(9):3495-3510).

Figure 2D:
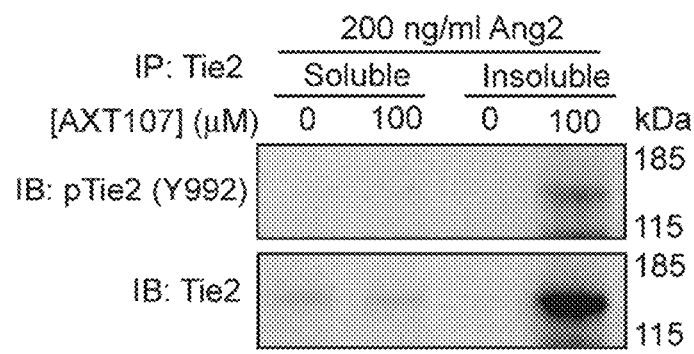
FIG. 2D is a representative image (n=3) of western blots of Triton X-100-fractionated lysates which were immunoprecipitated for Tie2 and blotted for phospho-Tie2 (top) or for total Tie2 (bottom).

Next, experiments were performed to determine whether or not relocation of Tie2 to the insoluble fraction was important for Tie2's activation by Ang2. Tie2 was immunoprecipitated from fractionated MEC lysates exposed to Ang2 with or without AXT107 and then immunoblotted for phospho-Tie2. Interestingly, phosphorylation was observed only in the insoluble fractions of peptide-treated samples (FIG. 2D).

These data demonstrate that treatment with AXT107 peptide results in the translocation of Tie2 to EC-EC junctions and activation of Tie2.

Figure 3A:
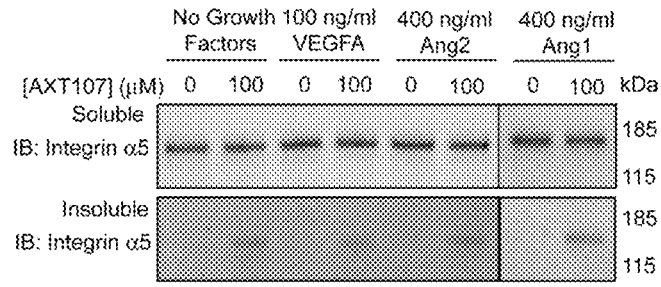
FIGS. 3A and 3C shows western blots of MEC lysates treated with various growth factors and 100 µM AXT107 or DMSO vehicle and fractioned into Triton X-100-soluble and Triton X-100-insoluble pools and immunoblotted for integrin $\alpha_5$ (A) or immunoblotted for integrin $\beta_1$ (C).
Figure 3B:
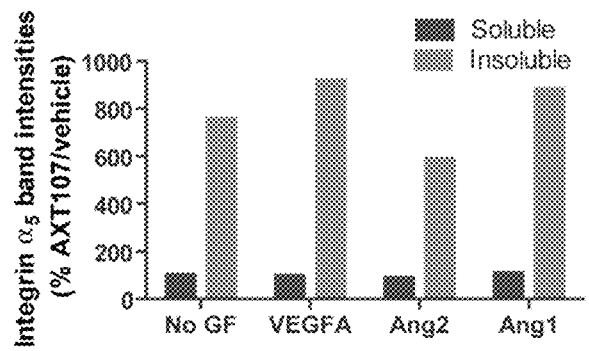
FIGS. 3B and 3D are graphs illustrating densitometric analyses of bands from, respectively, FIG. 3A and FIG. 3C; each bar represents the percent change of AXT107-treated samples relative to the corresponding vehicle control of the same growth factor and separated by soluble (left bars) and insoluble (right bars).

Example 3: AXT107 Disrupts Interactions Between α5 and β1 Integrin Subunits $α_5β_1$-integrin heterodimer and $α_vβ_3$-integrin heterodimer are primary targets of AXT107. To investigate the possibility of an integrin-mediated mechanism for regulating Tie2, fractionated MEC lysates immunoblotted for the $α_5$ integrin subunit revealed that a portion of the $α_5$ integrin subunit relocated to the insoluble fraction in samples treated with AXT107 (FIGS. 3A and 3B); this result is similar to what was observed for both Tie2 (FIG. 2D) and Tie1 (data not shown).

Figure 3C:
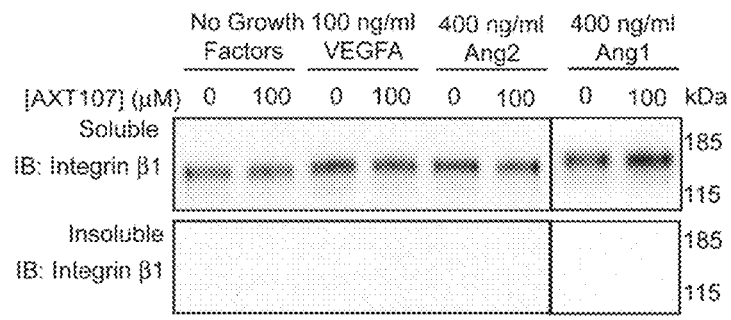
Figure 3D:
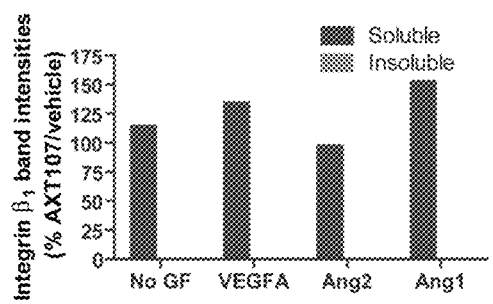
Figure 3E:
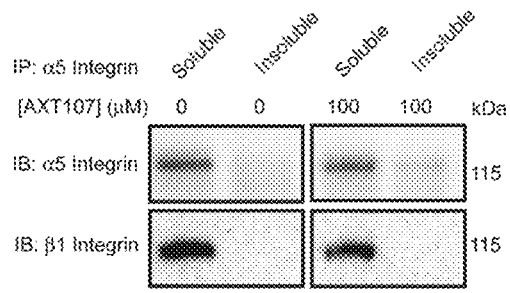
FIG. 3E shows western blots of Triton X-100-fractionated lysates which were immunoprecipitated for integrin $\alpha_5$ and blotted for integrin $\alpha_5$ (top) or for integrin $\beta_1$ (bottom).

Surprisingly, the $β_1$ integrin subunit was never observed in the insoluble fraction despite the use of long exposure times and high antibody concentrations (FIG. 3C to 3E). This suggests treatment with AXT107 disrupts the interaction between the $α_5$ integrin subunit and $β_1$ integrin subunit in an integrin heterodimer. Since $β_1$ integrin is the only known β subunit to heterodimerize with the $α_5$ integrin subunit, it unlikely that the $α_5$ subunit, that was observed here in the insoluble fractions, originated from a heterodimeric integrin pair other than $α_5β_1$. Unfortunately, high background impaired the visualization of $α_5$ integrin alone by immunofluorescence. Given the unexpected discovery that AXT107 dissociates the integrin heterodimer, this discovery was confirmed in several independent assays. Immunoprecipitation of $α_5$ integrin in Triton X-100 fractionated lysates revealed that while $α_5$ integrin could be observed in the insoluble fraction after AXT107 treatment, interactions with $β_1$ were only found in the soluble fractions (data not shown). Thus, interactions between Tie2 and heterodimerized $\alpha_5\beta_1$ integrin appear to retain Tie2 at the EC-ECM interface. This is consistent with reports that Tie2 does not interact with β1 integrin in absence of the α5 subunit (Cascone et al., *J Cell Biol.* 2005; 170(6):993-1004); disruption of these integrin heterodimers allow for the formation of Tie2-containing complexes at EC-EC junctions and in large clusters.

Figure 3F:
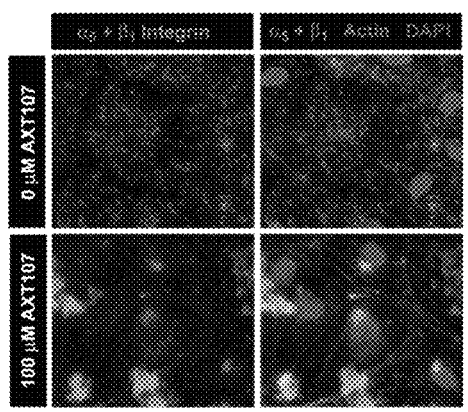
FIG. 3F shows photomicrographs of representative images of a Duolink™ assay showing interactions between $\alpha_5$ and $\beta_1$ integrins in MEC monolayers treated with vehicle or with 100 µM AXT107 and FIG. 3G is a graph quantifying the interactions per arbitrary area.
Figure 3G:
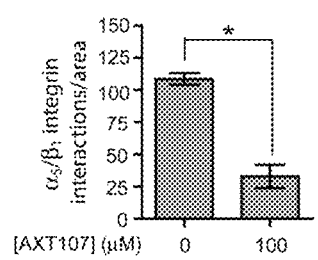

Additionally, changes in the interaction between the $\alpha_5$ and $\beta_1$ subunits were further investigated using Duolink™ technology which can visualize individual interactions between $\alpha_5$ and $\beta_1$ integrin subunits as distinct spots by fluorescence microscopy. Consistent with the results from the Triton X-100 fractionation studies (FIGS. 3A to 3E), interactions between $\alpha_5$ and $\beta_1$ integrin subunits were significantly reduced in monolayers treated with AXT107 compared to vehicle alone (FIGS. 3F and 3G).

Figure 3H:
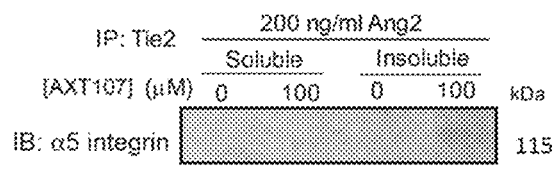
FIGS. 3H and 3I show representative images (n=3) of western blots of Triton X-100-fractionated lysates which were immunoprecipitated for Tie2 and blotted for α5 integrin; cells in FIG. 3H were treated with 200 ng/ml of Ang2 and cells in FIG. 3I were not treated with a growth factor. N=3.
Figure 3I:
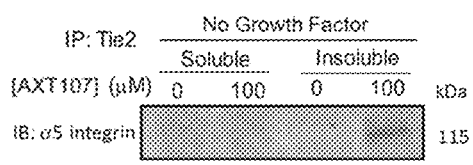

Finally, it was determined whether or not the $\alpha_5$ integrin subunit remains complexed with Tie2 following its disassociation with $\beta_1$ integrin. As shown in FIGS. 3H and 3I, $\alpha_5$ integrin was observed in the peptide-treated, insoluble fraction following immunoprecipitation of Tie2.

These data demonstrate that treatment with the AXT107 peptide dissociate α5 integrin and β1 integrin subunits from a heterodimer.

Interestingly, the knockdown of β1 integrin has been shown to decrease Akt phosphorylation; this contrasts the results from α5 integrin knockdown or peptide treatment. As a possible explanation, β1 is the most promiscuous of the integrins and decreases in its protein levels may impact more cellular activities, both Tie2-dependent and Tie2-independent, in comparison to knockdowns of the relatively-specific α5 integrin or conditions in which integrin levels remain constant but are inhibited. Taken together, these findings emphasize the importance of integrins in the preferential activation of signaling pathways downstream of Tie2.

Example 4: Treatment with AXT107 Strengthens and Narrows Endothelial Cell Junctions Having demonstrated that AXT107 potentiates the activation of Tie2 through the disruption of interactions between subunits in $\alpha_5\beta_1$ integrin, the following experiments were performed to determine the functional consequence of this activity.

Tie2 signaling is a major regulator of vascular permeability and dysfunction in this activity is known to contribute to increased macular edema and disease progression. Specifically, Tie2 strengthens cell-cell junctions through the formation of trans interactions with Tie2 receptors on adjacent cells and the reorganization of VE-Cadherin complexes continuously along cell-cell junctions.

Figure 4A:
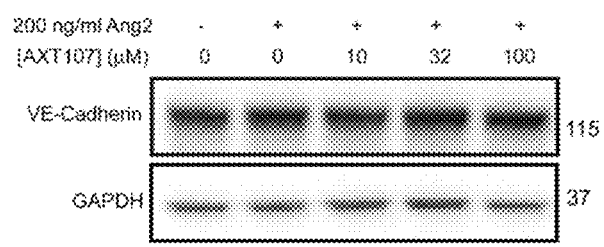
FIG. 4A shows a representative western blot of VE-Cadherin from MEC monolayers treated with 200 ng/ml Ang2 for three hours at various concentrations of AXT107; GAPDH is included as a loading control.
Figure 4B:
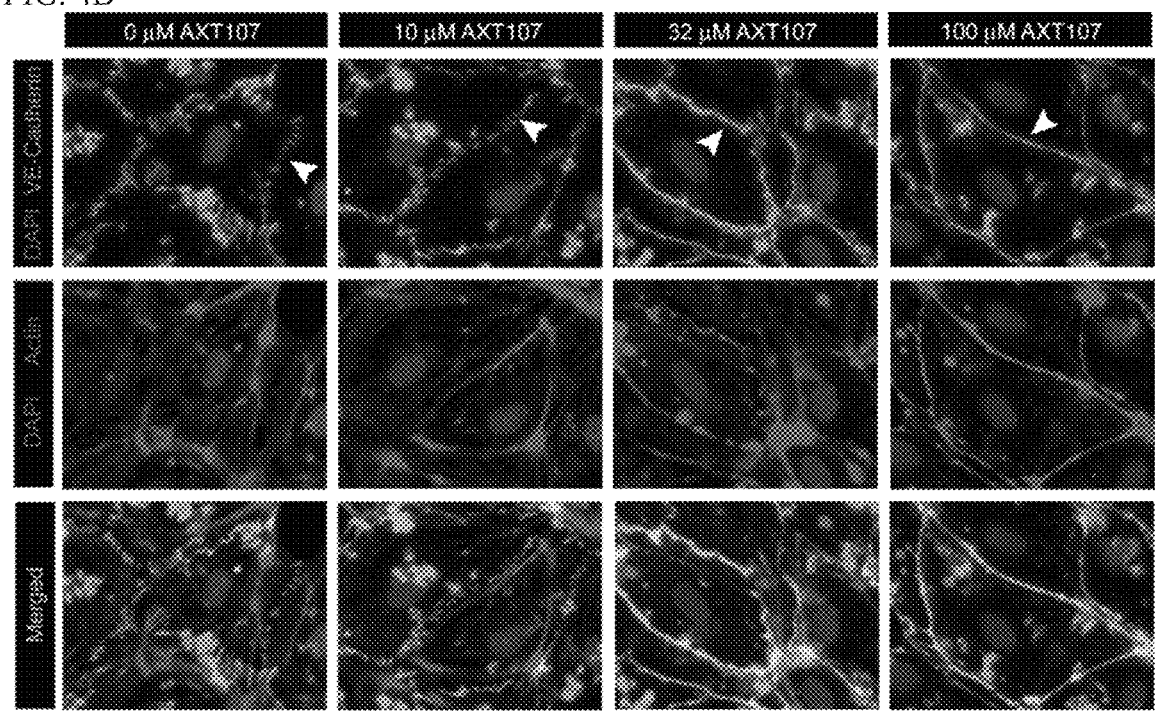
FIG. 4B shows photomicrographs of immunofluorescence images of MEC monolayers treated with 200 ng/ml Ang2 and various concentrations of AXT107 that have been stained with antibodies targeting VE-cadherin (green), F-actin (red), and DAPI (blue) and with merged regions shown in yellow; arrows indicate representative regions showing transition of VE-cadherin distribution.
Figure 4C:
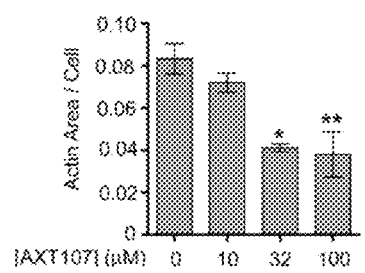
FIG. 4C is a graph quantifying the average area of F-actin coverage per cell; one-way ANOVA; N=3; *,  p≤0.05 and 0.01, respectively, relative to Ang2 alone control.

Consistent with previous reports of Tie2 activation by Ang1, the total level of VE-cadherin remained unchanged after three hours of AXT107 and Ang2 treatment (FIG. 4A). However, immunofluorescence imaging revealed clear changes in the structure of VE-cadherin junctions. As shown in FIG. 4B, at lower concentrations, the distribution of VE-cadherin was discontinuous and jagged in appearance but became progressively smoother with increasing concentrations of AXT107. The jaggedness of these junctions is related to the structure of actin within the cell. Absent AXT107 treatment (FIG. 4B, left column), radial actin fibers were arranged across the cells but became more cortical with increasing concentrations of AXT107 (compare with remaining columns in FIG. 4B; see, also, FIG. 4C). Radial actin functions to pull cells apart to increase permeability whereas junctional actin does not exert the same pull and thus results in decreased vascular permeability.

Figure 4D:
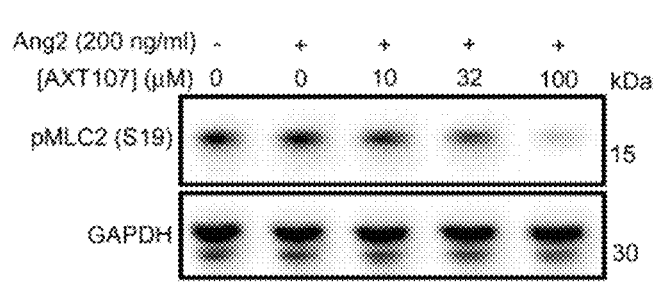
FIG. 4D shows representative western blot images of lysates from MECs treated with 200 ng/ml Ang2 and various concentrations of AXT107 blotted against pMLC2 and with GAPDH as a loading control.
Figure 4E:
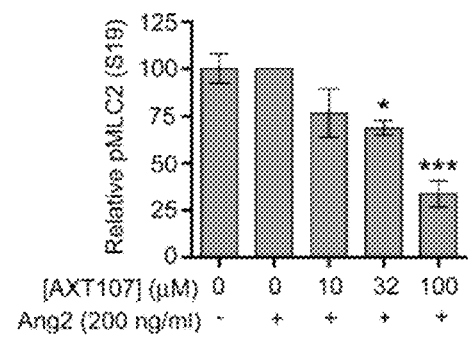
FIG. 4E is a graph showing a densitometric analysis of the data shown in FIG. 4D; one-way ANOVA; N=3; * p≤0.001 relative to Ang2-alone control.

Phosphorylation of Tie2 is known to stimulate the Rap1-GTPase pathway, leading to a reduction in the phosphorylation of the downstream motor protein myosin light chain 2 (MLC2) associated with actin rearrangement. As shown in FIG. 4D, phosphorylation of MLC2 is reduced in a dose-dependent manner following treatment with AXT107 and Ang2.

Figure 4F:
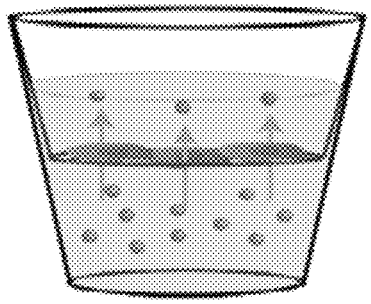
FIG. 4F is a schematic of transendothelial permeability assay described in Example 4.

The reorganization of VE-cadherin, actin, and Tie2 at endothelial cell junctions by AXT107 suggests that treatment with the peptide stabilizes cell-cell interactions. The integrity of these junctions is also important for the regulation of monolayer permeability by controlling the size of intercellular openings. The effect of the AXT107 on EC permeability was further investigated by the transendothelial diffusion of FITC-labeled dextran across MEC monolayers seeded onto permeable Transwell® substrates. A schematic of the assay is shown in FIG. 4F.

Figure 4G:
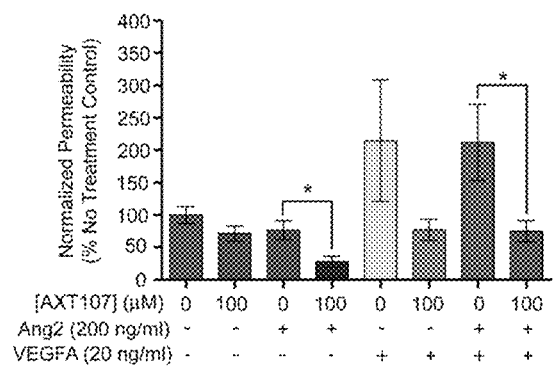
FIG. 4G is a graph showing quantification of FITC-Dextran (40 kDa) migration across MEC monolayers plated on semipermeable substrates following treatment with growth factors and AXT107, where indicated. Student's two-tailed t-test; N≥7; * p≤0.05.

As shown in FIG. 4G, treatment with Ang2 or AXT107 alone influenced FITC-dextran diffusion across the monolayer whereas VEGF treatment appeared to increase permeability (although non-significantly) alone or in combination with Ang2. Interestingly, the addition of Ang2 alone or in combination with VEGF to monolayers pre-incubated with 100 µM AXT107 showed a significant decrease in FITC-dextran diffusion into the top chamber when compared to cells treated with the growth factors alone. A similar, but non-significant trend was also observed between monolayers treated in VEGF in the presence and absence of peptide.

These data demonstrate that treatment with the AXT107 peptide results in decreased monolayer permeability through the reorganization of F-actin and VE-cadherin.

The importance of integrin interactions in the regulation of Tie2 signaling suggests that natural mechanisms may exist for this to occur within organisms. The treatment of ECs with cartilage oligomeric matrix protein (COMP)-Ang1 has been shown to induce junctional relocation of Tie2, suggesting that it may stimulate Tie2's dissociation from β1 integrin through a yet-unknown mechanism. Interestingly, differences in the C-termini of Ang1 and Ang2 were found to alter their interactions with β1 integrin which, consequently, could only be activated by Ang2.

Figure 5:
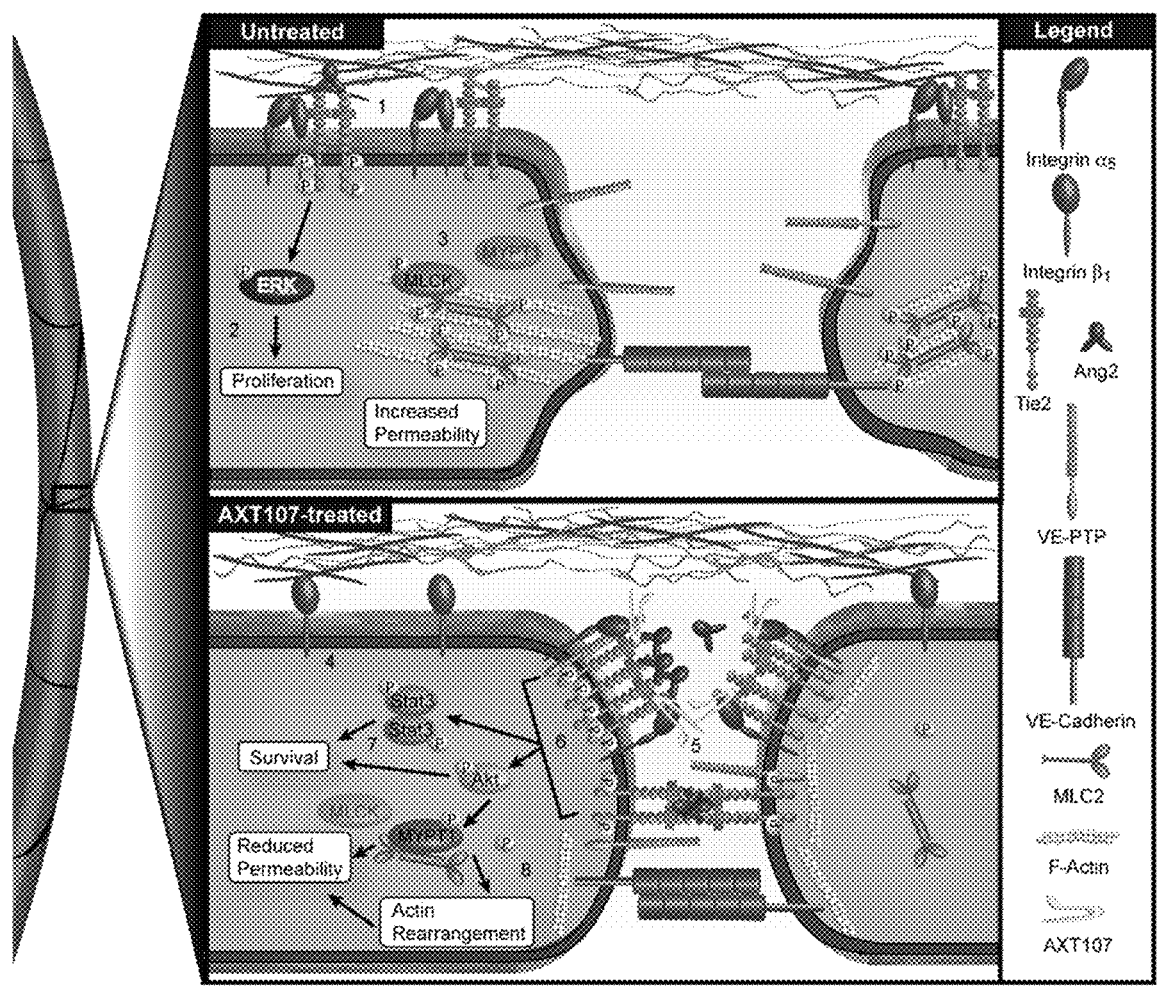
FIG. 5 includes a model for AXT107-mediated activation of Tie2.

Without wishing to be bound by theory, the data disclosed herein provide a model for AXT107-mediated activation of Tie2. As illustrated in FIG. 5, top, in the absence of AXT107 (1) Ang2 weakly activates Tie2 in complex with integrin $\alpha_5\beta_1$ heterodimers at the EC-ECM interface, which (2) preferentially activates proliferative signals (e.g., ERK1/2). (3) Active MLC kinase (MLCK) activates MLC3 and leads to formation of radial actin stress fibers within the cell and tension at EC-EC cell junctions. However, in the presence of AXT107, in FIG. 5, bottom, (4) $\alpha_5$ integrin separates from $\beta_1$ integrin and (5) migrates to EC-EC junctions along with Tie2 to form large complexes and/or trans-interactions across junctions. (6) These complexes potentiate the phosphorylation of Tie2 and activate (7) Akt- and STAT3-mediated survival pathways. Additionally, (8) MLC phosphatase is activated via a RAP1 or RAC1 pathway, which leads to reduced MLC2 activity, increased cortical actin, and stabilized junctions.

Example 5: In Vivo, the Exemplary Integrin-Binding, Biomimetic Potentiates Tie2 Phosphorylation To investigate the effects of AXT107 on Tie2 activation in vivo, retinopathy of prematurity (ROP) mouse model was used. In this system, P7 pups are placed in 75% $O_2$ for five days, resulting in a loss of retinal capillary density from hyperoxia and a rapid induction of neovascularization upon the pup's return to normoxic conditions. Here, the in vivo potential of the peptide was demonstrated using an eye vasculature model. Increased levels of Ang2 in the vitreous contribute to vessel leakage and macular edema in various retinopathies.

The Following Exemplary Methods and Materials were Used the Above Examples:

Cell Culture and Reagents

Human dermal microvascular endothelial cells (Lonza) were maintained at 37° C. and 5% $CO_2$ in EBM-2MV medium (Lonza) and used between passages two through seven. Where applicable, cells were serum starved in EBM-2 medium (Lonza) with no supplements. For FITC-Dextran permeability assays phenol red-free media were used to avoid auto-fluorescence. AXT107 were manufactured at New England Peptide by solid state synthesis, lyophilized, and dissolved in 100% DMSO. After dilution, preferably, DMSO concentrations did not exceed 0.25%.

Western Blotting

For Ang1/2 signaling investigations, cell culture dishes (10 cm diameter) were coated with 5 µg/ml fibronectin (FN1; Sigma-Aldrich, St. Louis, Mo.) for two hours at 37° C. The FN1 solution was then removed by aspiration and $5\times10^6$ microvascular endothelial cells (MECs; Lonza, Walkersville, Md.) were plated in EGM-2MV media (Lonza) and cultured for forty-eight hours at 37° C. The cells were then serum starved for sixteen hours in serum-free EGM-2 base media (Lonza). AXT107 (0-100 µM, as indicated) was subsequently added to each culture and incubated for seventy-five minutes at 37° C. The cultures were then treated with 1 mM sodium vanadate (New England Biolabs, Ipswich, Mass.) for fifteen minutes to enhance the phospho-Tie2 signal followed by stimulation with 200 ng/ml angiopoietin (R&D Systems, Minneapolis, Minn.) for an additional fifteen minutes. The cells were then transferred to ice, washed twice with ice cold Dulbecco's phosphate-buffered saline (dPBS) containing $Ca^{2+}$ and $Mg^{2+}$, and collected by scraping in 500 µl of 1× Blue Loading Buffer (Cell Signaling, Danvers, Mass.). Lysate samples were then sonicated, boiled, and resolved by SDS-PAGE. Specific proteins were identified by Western blot, using the following primary antibodies: Cell Signaling—phospho-Tie2 (Y992) (Cat #: 4221), Tie2 (Cat #: 7403), phospho-Stat3 (Y705) (Cat #: 4113), Stat3 (Cat #: 4904), phospho-Akt (S473) (Cat #: 4058), Akt (Cat #: 9272), phospho-p44/42 MAPK (T202/Y204) (Cat #: 4370), p44/42 MAPK (Cat #: 4695); BD Transduction Laboratories—$\beta_1$ integrin (Cat #: 610467); Millipore—$\alpha_5$ integrin (Cat #: AB1928) and detected with HRP-conjugated goat anti-rabbit and sheep anti-mouse secondary antibodies (GE healthcare).

Triton X-100 Fractionation

The isolation of Triton X-100 soluble and insoluble fractions was performed using modifications to previously-described procedures (see, e.g., Lampugnani et al., *J Cell Biol.* 1995; 129(1):203-217). FN1-coated six-well plates were seeded with $2.5\times10^6$ cells and cultured for forty-eight hours, as described above. The cultures were then serum starved for ninety minutes in EBM-2 media, treated with 100 µM AXT107 or DMSO vehicle, and fifteen minutes with 1 mM sodium vanadate. The cells were then stimulated with either 100 ng/ml VEGFA, 400 ng/ml Ang2, or PBS for fifteen minutes. The plates were then transferred to ice and washed twice with cold dPBS containing $Ca^{2+}$ and $Mg^{2+}$ and twice with EBM-2 media. The media was then removed and the cells incubated for thirty minutes on ice, at 4° C. in 200 µl of Triton X-100 extraction buffer (10 mM Tris-HCl, pH 7.5; 150 mM NaCl; 2 mM $CaCl_2$; 1% NP-40; 1% Triton C-100; and a protease inhibitor cocktail (Cell Signaling, Cat #: 5871)) with occasional agitation. The extraction buffer was gently collected and centrifuged at 12,000×g for five minutes. The supernatant was then mixed with 125 µl of 3× Blue Loading Dye, boiled, and saved as the Triton X-100 soluble fraction at −20° C. The remaining insoluble fraction was washed twice with wash buffer (10 mM Tris-HCl, pH 7.5; 150 mM NaCl; cOmplete™ Mini protease inhibitor tablets (Roche)) and collected in 375 µl of 1× Blue Loading Dye with scraping followed by centrifugation and boiling, as described above. This lysate was saved at −20° C. as the Triton X-100 insoluble fraction. Samples were analyzed by western blot as described above.

For pull-down variations, insoluble fractions were instead collected in RIPA buffer (Sigma) treated with a protease and phosphatase inhibitor cocktail (Cell Signaling) and 5 mM EDTA. Lysates were sonicated briefly and incubated for one hour with anti-Tie2 (Cell Signaling, Cat #: 4224) or anti-$\alpha_5$ integrin (Millipore; Cat #: AB1928) with end-over-end mixing. Subsequently, 20 µl of Protein Agarose A/G beads (Santa Cruz) were added and the samples incubated for another hour. Beads were collected by centrifugation at 1,500×g and 4° C., washed four times with PBS, resuspended in SDS-based Blue Loading Dye (Cell Signaling), boiled and resolved by SDS-PAGE.

Immunofluorescence

Glass-bottomed, 96-well plates with half well size were coated with 10 µg/ml FN1 for two hours at 37° C. The FN1 solution was then removed by aspiration and the plate seeded with $4\times10^3$ MECs in EGM-2MV media. After twenty-four hours, the cells were washed once with dPBS containing $Ca^{2+}$ and $Mg^{2+}$ to remove dead cells and the cells were allowed to grow for an additional twenty-four hours. For three-hour duration treatments (i.e., VE-cadherin), cells were washed twice with dPBS containing $Ca^{2+}$ and $Mg^{2+}$ and serum starved in EBM-2 for ninety minutes. The media was then removed and the cells were treated for three hours with 100 µl of EBM-2 media containing 200 ng/ml Ang2 or PBS and varying concentrations of AXT107 or DMSO. For fifteen minute-treated samples (i.e., phospho-Tie2), the cells were serum starved in EBM-2 media for 165 minutes, incubated for ninety minutes with varying concentrations of AXT107 or DMSO in EBM-2, and finally stimulated for fifteen minutes with 200 ng/ml Ang2 or PBS supplemented with peptide to retain the same concentrations. These times were chosen so that both treatment procedures would be completed at the same time. The cells were then washed twice with cold dPBS containing $Ca^{2+}$ and $Mg^{2+}$ and fixed in 10% neutral buffered formalin for fifteen minutes. The formalin solution was then removed, the wells washed three times in dPBS containing $Ca^{2+}$ and $Mg^{2+}$. The cells were then blocked in blocking buffer (5% normal goat serum; 0.3% Triton X-100 in dPBS containing $Ca^{2+}$ and $Mg^{2+}$) and stained for sixteen hours with primary antibodies for phospho-Tie2 (Y992) (R&D Systems; Cat #: AF2720) or VE-cadherin (Cell Signaling; Cat #: 2500) diluted 1:150 in antibody dilution buffer (1% BSA; 0.3% Triton X-100 in dPBS containing $Ca^{2+}$ and $Mg^{2+}$). The wells were then washed three times with dPBS and incubated for one hour with Alexafluor 488-conjugated goat anti-rabbit secondary antibodies (Cell Signaling; Cat #: 4412) diluted 1:300 in antibody dilution buffer. The wells were then washed twice and stained for twenty minutes with Alexafluor 555-conjugated phalloidin (Cell Signaling; Cat #: 8953) diluted 1:20 in PBS. The cells were then washed twice again in dPBS, stained with DAPI for twenty minutes, and solution exchanged with dPBS for imaging. Cells were imaged using the BD Pathway 855 system and Attovision software (BD Biosciences).

Duolink Protein Interaction Analysis

Glass bottom, 96-well plates were coated with FN1, seeded with MECs, as described above for the immunofluorescence experiments. After growing for forty-eight hours, cells were serum starved for three hours, treated with 100 µM AXT107 or DMSO vehicle for ninety minutes, washed twice with dPBS containing $Ca^{2+}$ and $Mg^{2+}$, and fixed in 10% neutral buffered formalin. Cells were blocked in 5% normal goat serum; 0.3% Triton X-100 in dPBS containing $Ca^{2+}$ and $Mg^{2+}$ for one hour and incubated overnight at 4° C. with rabbit anti-α5 integrin and mouse anti-β1 integrin antibodies in PBS containing $Ca^{2+}$ and $Mg^{2+}$ with 1% BSA and 0.1% Triton X-100. Interaction spots were developed using DUOLINK green detection reagent according to the manufacturer's instructions and detected using the BD pathway 855 system.

FITC Transwell Permeability Assay

Transwell, twenty-four-well inserts (Corning) were coated with 7.5 µg/cm$^2$ FN1 for two hours at 37° C., aspirated, and then dried for thirty minutes at room temperature. Wells were then seeded with 7.5×10$^4$ MECs in 100 µl of EBM-2 media (without phenol red) and allowed to settle for thirty minutes at room temperature. 1 ml of EGM-2 media was then added to the bottom chamber and an additional 200 µl to the top chamber. The plate was incubated for twenty-four hours at 37° C. after which the media was aspirated and an additional 7.5×10$^4$ MECs were plated in each well as described above. After forty-eight hours at 37° C., the media was aspirated from both chambers and the cells were washed twice in dPBS containing $Ca^{2+}$ and $Mg^{2+}$, once with EBM-2 media (without phenol red) and serum starved in EBM-2 media applied to both chambers for two hours at 37° C. After this incubation, 100 µM AXT107 or an equivalent amount of DMSO vehicle was added and incubated for an additional ninety minutes. In the top chamber, the cells were then treated with 200 ng/ml Ang2, 100 ng/ml VEGFA, both, or PBS control and in the bottom chamber, the cells were then treated with 25 µg/ml FITC-Dextran (40 kDa MW). AXT107 was also added in both chambers to maintain a concentration of 100 µM. After three hours, 10 µl was removed from the top chamber of each well and mixed with 90 µl of water in a clear bottom, 96-well plate. Fluorescence values for each sample were calculated using a Perkin Elmer plate reader.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties. Exemplary patent documents include WO 2007/033215, WO 2008/085828, WO 2010/132879, WO 2012/079088, WO 2014/197892, and WO 2017/087825 and those mentioned throughout the above-disclosure. Exemplary publications are listed below in the "REFERENCES" section and throughout the above-disclosure.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

1. Eklund L, Kangas J and Saharinen P. Angiopoietin-Tie signalling in the cardiovascular and lymphatic systems. Clin Sci (Lond). 2017; 131(1):87-103.
2. Saharinen P, Eklund L and Alitalo K. Therapeutic targeting of the angiopoietin-TIE pathway. Nat Rev Drug Discov. 2017.
3. Davis S, Aldrich T H, Jones P F, Acheson A, Compton D L, Jain V, Ryan T E, Bruno J, Radziejewski C, Maisonpierre P C and Yancopoulos G D. Isolation of angiopoietin-1, a ligand for the TIE2 receptor, by secretion-trap expression cloning. Cell. 1996; 87(7):1161-1169.
4. Saharinen P, Eklund L, Miettinen J, Wirkkala R, Anisimov A, Winderlich M, Nottebaum A, Vestweber D, Deutsch U, Koh G Y, Olsen B R and Alitalo K. Angiopoietins assemble distinct Tie2 signalling complexes in endothelial cell-cell and cell-matrix contacts. Nat Cell Biol. 2008; 10(5):527-537.
5. Frye M, Dierkes M, Kuppers V, Vockel M, Tomm J, Zeuschner D, Rossaint J, Zarbock A, Koh G Y, Peters K, Nottebaum A F and Vestweber D. Interfering with VE-PTP stabilizes endothelial junctions in vivo via Tie-2 in the absence of VE-cadherin. J Exp Med. 2015; 212(13): 2267-2287.
6. Dalton A C, Shlamkovitch T, Papo N and Barton W A. Constitutive Association of Tie1 and Tie2 with Endothelial Integrins is Functionally Modulated by Angiopoietin-1 and Fibronectin. PLoS One. 2016; 11(10): e0163732.
7. Fiedler U, Scharpfenecker M, Koidl S, Hegen A, Grunow V, Schmidt J M, Kriz W, Thurston G and Augustin H G. The Tie-2 ligand angiopoietin-2 is stored in and rapidly released upon stimulation from endothelial cell Weibel-Palade bodies. Blood. 2004; 103(11):4150-4156.
8. Maisonpierre P C, Suri C, Jones P F, Bartunkova S, Wiegand S J, Radziejewski C, Compton D, McClain J, Aldrich T H, Papadopoulos N, Daly T J, Davis S, Sato T N and Yancopoulos G D. Angiopoietin-2, a natural antagonist for Tie2 that disrupts in vivo angiogenesis. Science. 1997; 277(5322):55-60.
9. Benest A V, Kruse K, Savant S, Thomas M, Laib A M, Loos E K, Fiedler U and Augustin H G. Angiopoietin-2 is critical for cytokine-induced vascular leakage. PLoS One. 2013; 8(8):e70459.

10. Tabruyn S P, Colton K, Morisada T, Fuxe J, Wiegand S J, Thurston G, Coyle A J, Connor J and McDonald D M. Angiopoietin-2-driven vascular remodeling in airway inflammation. Am J Pathol. 2010; 177(6):3233-3243.
11. Daly C, Pasnikowski E, Burova E, Wong V, Aldrich T H, Griffiths J, Ioffe E, Daly T J, Fandl J P, Papadopoulos N, McDonald D M, Thurston G, Yancopoulos G D and Rudge J S. Angiopoietin-2 functions as an autocrine protective factor in stressed endothelial cells. Proc Natl Acad Sci USA. 2006; 103(42):15491-15496.
12. Yuan H T, Khankin E V, Karumanchi S A and Parikh S M. Angiopoietin 2 is a partial agonist/antagonist of Tie2 signaling in the endothelium. Mol Cell Biol. 2009; 29(8): 2011-2022.
13. Korhonen E A, Lampinen A, Giri H, Anisimov A, Kim M, Allen B, Fang S, D'Amico G, Sipila T J, Lohela M, Strandin T, Vaheri A, Yla-Herttuala S, Koh G Y, McDonald D M, Alitalo K, et al. Tie1 controls angiopoietin function in vascular remodeling and inflammation. J Clin Invest. 2016; 126(9):3495-3510.
14. Shen J, Frye M, Lee B L, Reinardy J L, McClung J M, Ding K, Kojima M, Xia H, Seidel C, Lima e Silva R, Dong A, Hackett S F, Wang J, Howard B W, Vestweber D, Kontos C D, et al. Targeting VE-PTP activates TIE2 and stabilizes the ocular vasculature. J Clin Invest. 2014; 124(10):4564-4576.
15. Singh H, Milner C S, Aguilar Hernandez M M, Patel N and Brindle N P. Vascular endothelial growth factor activates the Tie family of receptor tyrosine kinases. Cell Signal. 2009; 21(8):1346-1350.
16. Cascone I, Napione L, Maniero F, Serini G and Bussolino F. Stable interaction between alpha5beta1 integrin and Tie2 tyrosine kinase receptor regulates endothelial cell response to Ang-1. J Cell Biol. 2005; 170(6):993-1004.
17. Lee E, Lee S J, Koskimaki J E, Han Z, Pandey N B and Popel A S. Inhibition of breast cancer growth and metastasis by a biomimetic peptide. Sci Rep. 2014; 4:7139.
18. Lima E S R, Kanan Y, Mirando A C, Kim J, Shmueli R B, Lorenc V E, Fortmann S D, Sciamanna J, Pandey N B, Green J J, Popel A S and Campochiaro P A. Tyrosine kinase blocking collagen IV-derived peptide suppresses ocular neovascularization and vascular leakage. Sci Transl Med. 2017; 9(373).
19. Karagiannis E D and Popel A S. A systematic methodology for proteome-wide identification of peptides inhibiting the proliferation and migration of endothelial cells. Proc Natl Acad Sci USA. 2008; 105(37):13775-13780.
20. Chen T T, Luque A, Lee S, Anderson S M, Segura T and Iruela-Arispe M L. Anchorage of VEGF to the extracellular matrix conveys differential signaling responses to endothelial cells. J Cell Biol. 2010; 188(4):595-609.
21. Soldi R, Mitola S, Strasly M, Defilippi P, Tarone G and Bussolino F. Role of alphavbeta3 integrin in the activation of vascular endothelial growth factor receptor-2. EMBO J. 1999; 18(4):882-892.
22. Veevers-Lowe J, Ball S G, Shuttleworth A and Kielty C M. Mesenchymal stem cell migration is regulated by fibronectin through alpha5beta1-integrin-mediated activation of PDGFR-beta and potentiation of growth factor signals. J Cell Sci. 2011; 124(Pt 8):1288-1300.
23. Rahman S, Patel Y, Murray J, Patel K V, Sumathipala R, Sobel M and Wijelath E S. Novel hepatocyte growth factor (HGF) binding domains on fibronectin and vitronectin coordinate a distinct and amplified Met-integrin induced signalling pathway in endothelial cells. BMC Cell Biol. 2005; 6(1):8.
24. Baron V and Schwartz M. Cell adhesion regulates ubiquitin-mediated degradation of the platelet-derived growth factor receptor beta. J Biol Chem. 2000; 275(50): 39318-39323.
25. Campochiaro P A, Khanani A, Singer M, Patel S, Boyer D, Dugel P, Kherani S, Withers B, Gambino L, Peters K, Brigell M and Group T-S. Enhanced Benefit in Diabetic Macular Edema from AKB-9778 Tie2 Activation Combined with Vascular Endothelial Growth Factor Suppression. Ophthalmology. 2016; 123(8):1722-1730.
26. Orfanos S E, Kotanidou A, Glynos C, Athanasiou C, Tsigkos S, Dimopoulou I, Sotiropoulou C, Zakynthinos S, Armaganidis A, Papapetropoulos A and Roussos C. Angiopoietin-2 is increased in severe sepsis: correlation with inflammatory mediators. Crit Care Med. 2007; 35(1): 199-206.
27. Ziegler T, Horstkotte J, Schwab C, Pfetsch V, Weinmann K, Dietzel S, Rohwedder I, Hinkel R, Gross L, Lee S, Hu J, Soehnlein O, Franz W M, Sperandio M, Pohl U, Thomas M, et al. Angiopoietin 2 mediates microvascular and hemodynamic alterations in sepsis. J Clin Invest. 2013.
28. Han S, Lee S J, Kim K E, Lee H S, Oh N, Park I, Ko E, Oh S J, Lee Y S, Kim D, Lee S, Lee D H, Lee K H, Chae S Y, Lee J H, Kim S J, et al. Amelioration of sepsis by TIE2 activation-induced vascular protection. Sci Transl Med. 2016; 8(335):335ra355.
29. Lampugnani M G, Corada M, Caveda L, Breviario F, Ayalon O, Geiger B and Dejana E. The molecular organization of endothelial cell to cell junctions: differential association of plakoglobin, beta-catenin, and alpha-catenin with vascular endothelial cadherin (VE-cadherin). J Cell Biol. 1995; 129(1):203-217.

What is claimed is:

1. A method for preparing a pharmaceutical composition, comprising:
contacting a candidate α- or β-integrin-binding molecule, or a panel of candidate α- or β-integrin-binding molecules, with a integrin heterodimer, wherein the integrin heterodimer is $α_5β_1$ and/or $α_vβ_3$, and quantifying heterodimer disruption by the candidate molecule; wherein quantifying heterodimer disruption comprises detecting or quantifying dissociation of the integrin heterodimer into its α integrin subunit and its β integrin subunit;
selecting an integrin-binding molecule that disrupts the integrin heterodimer; and
formulating the integrin disrupting molecule for administration to a subject, thereby preparing the pharmaceutical composition.

2. The method of claim 1, wherein quantifying heterodimer disruption is further determined by quantifying Tyrosine Kinase With Immunoglobulin Like And EGF Like Domains 1 (Tie1) and/or Tyrosine Kinase With Immunoglobulin Like And EGF Like Domains 2 (Tie2) activation.

3. The method of claim 2, wherein quantifying Tie1 and/or Tie2 activation comprises assaying changes in phosphorylation or activity of Tie1 and/or Tie2.

4. The method of claim 2, wherein quantifying Tie1 and/or Tie2 activation comprises assaying changes in phosphorylation or activity of signaling molecules associated with Tie1 and/or Tie2.

5. The method of claim 4, wherein the signaling molecules associated with Tie1 and/or Tie2 comprise Protein kinase B (Akt) or Signal transducer and activator of transcription 3 (STAT3).

6. The method of claim 2, wherein quantifying Tie1 and/or Tie2 activation comprises assaying changes in phosphorylation or activity of protein myosin light chain 2 (MLC2).

7. The method of claim 2, wherein quantifying Tie1 and/or Tie2 activation comprises assaying changes in tyrosine kinase activity.

8. The method of claim 7, wherein assaying changes in tyrosine kinase activity comprises contacting Tie1 and/or Tie2 with an exogenous substrate in the presence of ATP.

9. The method of claim 2, wherein quantifying Tie1 and/or Tie2 activation comprises detecting or quantifying clustering of Tie1 and/or Tie2.

10. The method of claim 1, wherein quantifying heterodimer disruption further comprises detecting formation of and reorganization of cadherin complexes.

11. The method of claim 1, wherein at least one step comprises one or more of: bimolecular fluorescence complementation (BiFC), proximity-dependent biotin identification (BioID), *Escherichia coli* biotin ligase (BirA), co-immunoprecipitation, crosslinking protein interaction analysis, dark quenching, detergent fractionation, far-Western blot analysis, fluorescence co-localization, fluorescence resonance energy transfer (FRET), immuno electron microscopy, immuno precipitation, label transfer, proximity ligation assay, pull-down assays, and a split-ubiquitin system.

12. The method of claim 2, wherein the Tie2 activation is angiopoietin 2 (Ang2)-dependent.

13. The method of claim 1, wherein the candidate molecule comprises a peptide or a polypeptide.

14. The method of claim 13, wherein the peptide comprises the amino acid sequence of SEQ ID NO:1 or a derivative thereof.

15. The method of claim 14, wherein the peptide comprises a derivative of SEQ ID NO:2.

* * * * *

SEQUENCE LISTING

```
<160> NUMBER OF SEQ ID NOS: 37

<210> SEQ ID NO 1
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: X is M, A, or G
<220> FEATURE:
<221> NAME/KEY: MISC_FEATURE
<222> LOCATION: (9)..(9)
```

```
<223> OTHER INFORMATION: X is F, A, Y, or G
<220> FEATURE:
<221> NAME/KEY: MISC_FEATURE
<222> LOCATION: (10)..(10)
<223> OTHER INFORMATION: X is M, A, G, dA, or Nle
<220> FEATURE:
<221> NAME/KEY: MISC_FEATURE
<222> LOCATION: (11)..(11)
<223> OTHER INFORMATION: X is F, A, Y, G, or 4-ClPhe
<220> FEATURE:
<221> NAME/KEY: MISC_FEATURE
<222> LOCATION: (12)..(12)
<223> OTHER INFORMATION: X is Abu, G, S, A, V, T, I, L or Allyl-Gly
<220> FEATURE:
<221> NAME/KEY: MISC_FEATURE
<222> LOCATION: (18)..(18)
<223> OTHER INFORMATION: X is Abu, G, S, A, V, T, I, L or Allyl-Gly

<400> SEQUENCE: 1

Leu Arg Arg Phe Ser Thr Xaa Pro Xaa Xaa Xaa Xaa Asn Ile Asn Asn
1               5                   10                  15

Val Xaa Asn Phe
        20

<210> SEQ ID NO 2
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 2

Leu Arg Arg Phe Ser Thr Ala Pro Phe Ala Phe Ile Asp Ile Asn Asp
1               5                   10                  15

Val Ile Asn Phe
        20

<210> SEQ ID NO 3
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 3

Leu Arg Arg Phe Ser Thr Ala Pro Phe Ala Phe Ile Asn Ile Asn Asn
1               5                   10                  15

Val Ile Asn Phe
        20

<210> SEQ ID NO 4
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 4

Leu Arg Arg Phe Ser Thr Ala Pro Phe Ala Phe Ile Asp Ile Asn Asp
1               5                   10                  15

Val Ile Asn Trp
        20

<210> SEQ ID NO 5
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 5

Phe Thr Asn Ile Asn Asn Val Thr Asn
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 6

Phe Thr Asp Ile Asn Asp Val Thr Asn
1               5

<210> SEQ ID NO 7
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (12)..(12)
<223> OTHER INFORMATION: X is Abu
<220> FEATURE:
<221> NAME/KEY: MISC_FEATURE
<222> LOCATION: (18)..(18)
<223> OTHER INFORMATION: X is Abu

<400> SEQUENCE: 7

Leu Arg Arg Phe Ser Thr Met Pro Phe Met Phe Xaa Asn Ile Asn Asn
1               5                   10                  15

Val Xaa Asn Phe
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (12)..(12)
<223> OTHER INFORMATION: X is Abu
<220> FEATURE:
<221> NAME/KEY: MISC_FEATURE
<222> LOCATION: (18)..(18)
<223> OTHER INFORMATION: X is Abu

<400> SEQUENCE: 8

Leu Arg Arg Phe Ser Thr Met Pro Ala Met Phe Xaa Asn Ile Asn Asn
1               5                   10                  15

Val Xaa Asn Phe
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (12)..(12)
```

```
<223> OTHER INFORMATION: X is Abu
<220> FEATURE:
<221> NAME/KEY: MISC_FEATURE
<222> LOCATION: (18)..(18)
<223> OTHER INFORMATION: X is Abu

<400> SEQUENCE: 9

Leu Arg Arg Phe Ser Thr Met Pro Phe Ala Phe Xaa Asn Ile Asn Asn
1               5                   10                  15

Val Xaa Asn Phe
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (12)..(12)
<223> OTHER INFORMATION: X is Abu
<220> FEATURE:
<221> NAME/KEY: MISC_FEATURE
<222> LOCATION: (18)..(18)
<223> OTHER INFORMATION: X is Abu

<400> SEQUENCE: 10

Leu Arg Arg Phe Ser Thr Met Pro Phe Met Ala Xaa Asn Ile Asn Asn
1               5                   10                  15

Val Xaa Asn Phe
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (10)..(10)
<223> OTHER INFORMATION: X is Nle
<220> FEATURE:
<221> NAME/KEY: MISC_FEATURE
<222> LOCATION: (12)..(12)
<223> OTHER INFORMATION: X is Abu
<220> FEATURE:
<221> NAME/KEY: MISC_FEATURE
<222> LOCATION: (18)..(18)
<223> OTHER INFORMATION: X is Abu

<400> SEQUENCE: 11

Leu Arg Arg Phe Ser Thr Met Pro Phe Xaa Phe Xaa Asn Ile Asn Asn
1               5                   10                  15

Val Xaa Asn Phe
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (11)..(11)
<223> OTHER INFORMATION: X is 4-ClPhe
<220> FEATURE:
<221> NAME/KEY: MISC_FEATURE
```

```
<222> LOCATION: (12)..(12)
<223> OTHER INFORMATION: X is Abu
<220> FEATURE:
<221> NAME/KEY: MISC_FEATURE
<222> LOCATION: (18)..(18)
<223> OTHER INFORMATION: X is Abu

<400> SEQUENCE: 12

Leu Arg Arg Phe Ser Thr Met Pro Phe Met Xaa Xaa Asn Ile Asn Asn
1               5                  10                 15

Val Xaa Asn Phe
         20

<210> SEQ ID NO 13
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 13

Leu Arg Arg Phe Ser Thr Met Pro Phe Met Phe Ser Asn Ile Asn Asn
1               5                  10                 15

Val Ser Asn Phe
         20

<210> SEQ ID NO 14
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 14

Leu Arg Arg Phe Ser Thr Met Pro Phe Met Phe Ala Asn Ile Asn Asn
1               5                  10                 15

Val Ala Asn Phe
         20

<210> SEQ ID NO 15
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 15

Leu Arg Arg Phe Ser Thr Met Pro Phe Met Phe Ile Asn Ile Asn Asn
1               5                  10                 15

Val Ile Asn Phe
         20

<210> SEQ ID NO 16
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 16

Leu Arg Arg Phe Ser Thr Met Pro Phe Met Phe Thr Asn Ile Asn Asn
1               5                  10                 15

Val Thr Asn Phe
         20
```

```
<210> SEQ ID NO 17
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (12)..(12)
<223> OTHER INFORMATION: X is AllyGly
<220> FEATURE:
<221> NAME/KEY: MISC_FEATURE
<222> LOCATION: (18)..(18)
<223> OTHER INFORMATION: X is AllyGly

<400> SEQUENCE: 17

Leu Arg Arg Phe Ser Thr Met Pro Phe Met Phe Xaa Asn Ile Asn Asn
1               5                   10                  15

Val Xaa Asn Phe
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 18

Leu Arg Arg Phe Ser Thr Met Pro Phe Met Phe Val Asn Ile Asn Asn
1               5                   10                  15

Val Val Asn Phe
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (10)..(10)
<223> OTHER INFORMATION: X is dA

<400> SEQUENCE: 19

Leu Arg Arg Phe Ser Thr Met Pro Phe Xaa Phe Ile Asn Ile Asn Asn
1               5                   10                  15

Val Ile Asn Phe
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 20

Leu Arg Arg Phe Ser Thr Met Pro Phe Ala Phe Ile Asn Ile Asn Asn
1               5                   10                  15

Val Ile Asn Phe
            20

<210> SEQ ID NO 21
<211> LENGTH: 20
```

```
<212> TYPE: PRT
<213> ORGANISM: Artificial Sequence
<220> FEATURE:
<223> OTHER INFORMATION: Synthetic Peptide

<400> SEQUENCE: 21

Leu Arg Arg Phe Ser Thr Ala Pro Phe Ala Phe Ile Asn Ile Asn Asn
1               5                   10                  15

Val Ile Asn Phe
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (10)..(10)
<223> OTHER INFORMATION: X is dA

<400> SEQUENCE: 22

Leu Arg Arg Phe Ser Thr Ala Pro Phe Xaa Phe Ile Asp Ile Asn Asp
1               5                   10                  15

Val Ile Asn Phe
            20

<210> SEQ ID NO 23
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is Abu
<220> FEATURE:
<221> NAME/KEY: MISC_FEATURE
<222> LOCATION: (8)..(8)
<223> OTHER INFORMATION: X is Abu

<400> SEQUENCE: 23

Phe Xaa Asn Ile Asn Asn Val Xaa Asn
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 24

Phe Thr Asn Ile Asn Asn Val Thr Asn
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 25

Phe Ile Asn Ile Asn Asn Val Ile Asn Phe
1               5                   10
```

```
<210> SEQ ID NO 26
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 26

Phe Ser Asn Ile Asn Asn Val Ser Asn Phe
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 27

Phe Ala Asn Ile Asn Asn Val Ala Asn Phe
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is AllyGly
<220> FEATURE:
<221> NAME/KEY: MISC_FEATURE
<222> LOCATION: (8)..(8)
<223> OTHER INFORMATION: X is AllyGly

<400> SEQUENCE: 28

Phe Xaa Asn Ile Asn Asn Val Xaa Asn Phe
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 29

Phe Val Asn Ile Asn Asn Val Val Asn Phe
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is Abu
<220> FEATURE:
<221> NAME/KEY: MISC_FEATURE
<222> LOCATION: (8)..(8)
<223> OTHER INFORMATION: X is Abu

<400> SEQUENCE: 30
```

Ala Xaa Asn Ile Asn Asn Val Xaa Asn Phe
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is 4-ClPhe
<220> FEATURE:
<221> NAME/KEY: MISC_FEATURE
<222> LOCATION: (2)..(2)
<223> OTHER INFORMATION: X is Abu
<220> FEATURE:
<221> NAME/KEY: MISC_FEATURE
<222> LOCATION: (8)..(8)
<223> OTHER INFORMATION: X is Abu

<400> SEQUENCE: 31

Xaa Xaa Asn Ile Asn Asn Val Xaa Asn Phe
1               5                   10

<210> SEQ ID NO 32
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is dL
<220> FEATURE:
<221> NAME/KEY: MISC_FEATURE
<222> LOCATION: (4)..(4)
<223> OTHER INFORMATION: X is dL

<400> SEQUENCE: 32

Xaa Arg Arg Xaa Arg Arg Phe Ser Thr Ala Pro Phe Ala Phe Ile Asp
1               5                   10                  15

Ile Asn Asp Val Ile Asn Phe
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is dL
<220> FEATURE:
<221> NAME/KEY: MISC_FEATURE
<222> LOCATION: (20)..(20)
<223> OTHER INFORMATION: X is dF

<400> SEQUENCE: 33

Xaa Arg Arg Phe Ser Thr Ala Pro Phe Ala Phe Ile Asp Ile Asn Asp
1               5                   10                  15

Val Ile Asn Xaa
            20

<210> SEQ ID NO 34
<211> LENGTH: 10

```
<212> TYPE: PRT
<213> ORGANISM: Artificial Sequence
<220> FEATURE:
<223> OTHER INFORMATION: Synthetic Peptide

<400> SEQUENCE: 34

Phe Ile Asp Ile Asn Asp Val Ile Asn Phe
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 35

Phe Ile Asp Ile Asn Asp Val Ile Asn Trp
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 36

Phe Thr Asp Ile Asn Asp Val Thr Asn
1               5

<210> SEQ ID NO 37
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (20)..(20)
<223> OTHER INFORMATION: X is dF

<400> SEQUENCE: 37

Leu Arg Arg Phe Ser Thr Ala Pro Phe Ala Phe Ile Asp Ile Asn Asp
1               5                   10                  15

Val Ile Asn Xaa
            20
```